United States Patent
Firlik et al.

(10) Patent No.: US 8,019,425 B2
(45) Date of Patent: Sep. 13, 2011

(54) METHODS AND APPARATUS FOR EFFECTUATING A LASTING CHANGE IN A NEURAL-FUNCTION OF A PATIENT

(75) Inventors: Andrew D. Firlik, New Canaan, CT (US); Jeffrey Balzer, Allison Park, PA (US); Alan J. Levy, Bellevue, WA (US); Bradford Evan Gliner, Sammamish, WA (US); Katrina S. Firlik, New Canaan, CT (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 469 days.

(21) Appl. No.: 12/343,454

(22) Filed: Dec. 23, 2008

(65) Prior Publication Data

US 2009/0171416 A1    Jul. 2, 2009

Related U.S. Application Data

(63) Continuation of application No. 10/913,183, filed on Aug. 6, 2004, now abandoned, which is a continuation of application No. 10/606,202, filed on Jun. 24, 2003, now Pat. No. 7,672,730, which is a continuation-in-part of application No. 09/802,808, filed on Mar. 8, 2001, now Pat. No. 7,010,351.

(60) Provisional application No. 60/217,981, filed on Jul. 13, 2000.

(51) Int. Cl.
    *A61N 1/00*    (2006.01)
(52) U.S. Cl. ......................................................... 607/45
(58) Field of Classification Search ....................... 607/45
    See application file for complete search history.

(56) References Cited

U.S. PATENT DOCUMENTS 6,463,328 B1 * 10/2002 John ............................... 607/45

* cited by examiner

*Primary Examiner* — George Manuel
(74) *Attorney, Agent, or Firm* — Melissa Acosta; Christopher S.L. Crawford; Craig Hoersten

(57) ABSTRACT

Methods and apparatus for treating an impaired neural function in a brain of a patient. In one embodiment, a method for treating a neural function in a brain of a patient includes determining a therapy period during which a plurality of therapy sessions are to be performed to recover functional ability corresponding to the neural function. The method continues by identifying a stimulation site in or on the brain of the patient associated with the neural function, and positioning an electrode at least proximate to the identified stimulation site. The patient is then treated by providing electrical stimulation treatments to the stimulation site. The treatment can comprise delivering electrical stimulation signals to the electrode during the therapy sessions. After expiration of the therapy period, the method includes preventing electrical stimulation signals from being delivered to the stimulation site.

15 Claims, 21 Drawing Sheets

METHODS AND APPARATUS FOR EFFECTUATING A LASTING CHANGE IN A NEURAL-FUNCTION OF A PATIENT

CROSS-REFERENCE TO RELATED APPLICATIONS

This is application is a continuation of U.S. application Ser. No. 10/913,183 filed Aug. 6, 2004 which is a continuation of U.S. application Ser. No. 10/606,202 filed Jun. 24, 2003, which is a Continuation-in-Part of U.S. application Ser. No. 09/802,808, filed Mar. 8, 2001.

TECHNICAL FIELD

Several embodiments of methods and apparatus in accordance with the invention are related to electrically stimulating a region in the cortex or other area of the brain for a limited treatment period to bring about a lasting change in a physiological function and/or a mental process of a patient.

BACKGROUND

A wide variety of mental and physical processes are controlled or influenced by neural activity in particular regions of the brain. For example, the neural-functions in some areas of the brain (i.e., the sensory or motor cortices) are organized according to physical or cognitive functions. There are also several other areas of the brain that appear to have distinct functions in most individuals. In the majority of people, for example, the areas of the occipital lobes relate to vision, the regions of the left interior frontal lobes relate to language, and the regions of the cerebral cortex appear to be consistently involved with conscious awareness, memory, and intellect.

Many problems or abnormalities can be caused by damage, disease and/or disorders in the brain. Effectively treating such abnormalities may be very difficult. For example, a stroke is a common condition that damages the brain. Strokes are generally caused by emboli (e.g., obstruction of a vessel), hemorrhages (e.g., rupture of a vessel), or thrombi (e.g., clotting) in the vascular system of a specific region of the brain. Such events generally result in a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus an adjunctive therapy such as amphetamine treatment. For most patients, however, such treatments are minimally effective and little can be done to improve the function of an affected body part beyond the recovery that occurs naturally without intervention. As a result, many types of physical and/or cognitive deficits that remain after treating neurological damage or disorders are typically considered permanent conditions that patients must manage for the remainder of their lives.

Neurological problems or abnormalities are often related to electrical and/or chemical activity in the brain. Neural activity is governed by electrical impulses or "action potentials" generated in neurons and propagated along synoptically connected neurons. When a neuron is in a quiescent state, it is polarized negatively and exhibits a resting membrane potential typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials when the integration exceeds a threshold potential. A neural firing threshold, for example, may be approximately −55 mV.

It follows that neural activity in the brain can be influenced by electrical energy supplied from an external source such as a waveform generator. Various neural functions can be promoted or disrupted by applying an electrical current to the cortex or other region of the brain. As a result, researchers have attempted to treat physical damage, disease and disorders in the brain using electrical or magnetic stimulation signals to control or affect brain functions.

Transcranial electrical stimulation (TES) is one such approach that involves placing an electrode on the exterior of the scalp and delivering an electrical current to the brain through the scalp and skull. Another treatment approach, transcranial magnetic stimulation (TMS), involves producing a magnetic field adjacent to the exterior of the scalp over an area of the cortex. Yet another treatment approach involves direct electrical stimulation of neural tissue using implanted electrodes.

The neural stimulation signals used by these approaches may comprise a series of electrical or magnetic pulses that can affect neurons within a target neural population. Stimulation signals may be defined or described in accordance with stimulation signal parameters including pulse amplitude, pulse frequency, duty cycle, stimulation signal duration, and/or other parameters. Electrical or magnetic stimulation signals applied to a population of neurons can depolarize neurons within the population toward their threshold potentials. Depending upon stimulation signal parameters, this depolarization can cause neurons to generate or fire action potentials. Neural stimulation that elicits or induces action potentials in a functionally significant proportion of the neural population to which the stimulation is applied is referred to as suprathreshold stimulation; neural stimulation that fails to elicit action potentials in a functionally significant proportion of the neural population is defined as sub-threshold stimulation. In general, supra-threshold stimulation of a neural population triggers or activates one or more functions associated with the neural population, but sub-threshold stimulation by itself does not trigger or activate such functions. Supra-threshold neural stimulation can induce various types of measurable or monitorable responses in a patient. For example, suprathreshold stimulation applied to a patient's motor cortex can induce muscle fiber contractions in an associated part of the body.

Although electrical or magnetic stimulation of neural tissue may be directed toward producing an intended type of therapeutic, rehabilitative, or restorative neural activity, such stimulation may result in collateral neural activity. In particular, neural stimulation delivered beyond a certain intensity, period of time, level, or amplitude can give rise to seizure activity and/or other types of collateral activity. It will be appreciated that collateral neural activity may be undesirable and/or inconvenient in a neural stimulation situation.

Conventional neural stimulation systems and techniques are generally directed toward treating or managing chronic patient symptoms on a perpetual or essentially perpetual basis, i.e., throughout a patient's lifespan. Therefore, conventional neural stimulation systems and methods may not be ideally suited for applications directed toward restoring rather than perpetually treating impaired functions.

DETAILED DESCRIPTION

Figure 1A:
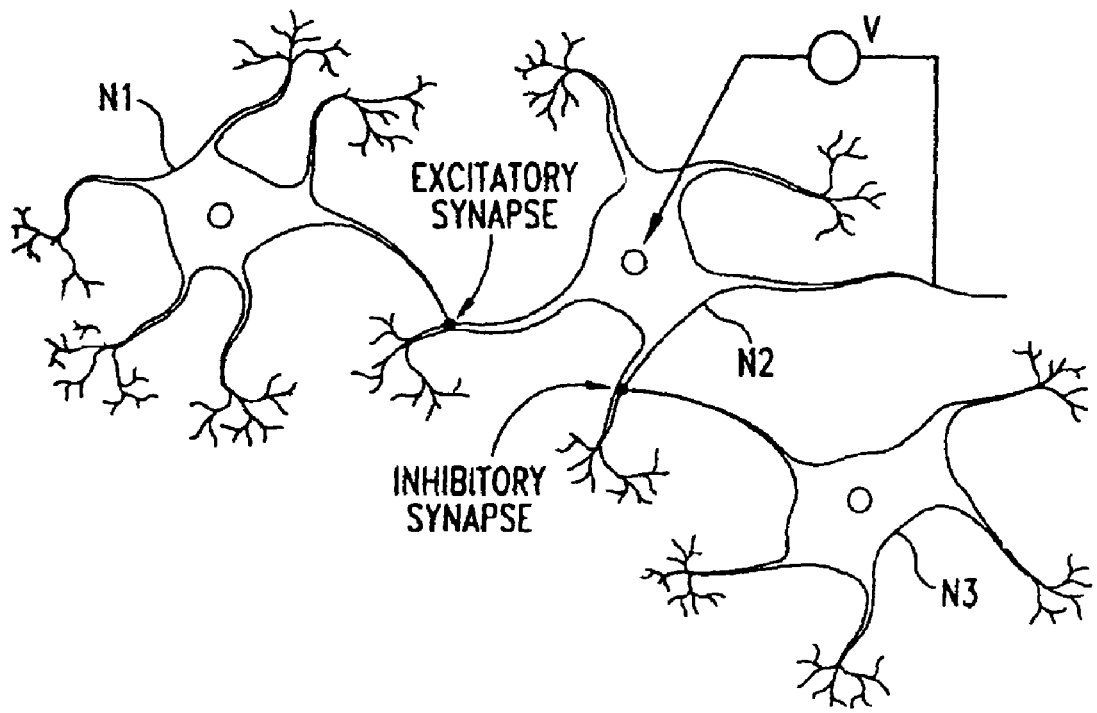
FIG. 1A is a schematic illustration of neurons.

The following disclosure describes several methods and apparatus for intracranial electrical stimulation to treat or otherwise effectuate a change in neural-functions of a patient. Several embodiments of methods described herein are directed toward enhancing or otherwise inducing neuroplasticity to effectuate a particular neural-function. Neuroplasticity refers to the ability of the brain to change or adapt over time. It was once thought adult brains became relatively "hard wired" such that functionally significant neural networks could not change significantly over time or in response to injury. It has become increasingly more apparent that these neural networks can change and adapt over time so that meaningful function can be restored in response to brain injury. An aspect of several embodiments of methods in accordance with the invention is to provide the appropriate triggers for adaptive neuroplasticity. These appropriate triggers appear to cause or enable increased synchrony of functionally significant populations of neurons in a network.

Neural stimulation applied or delivered in various manners described herein may excite a portion of a neural network involved in or associated with a functionally significant task such that a selected population of neurons can become more strongly associated with that network. Because such a network will subserve a functionally meaningful task, such as motor relearning, the changes are more likely to be lasting because they are continually being reinforced by natural use mechanisms. The nature of stimulation in accordance with several embodiments of the invention ensures that the stimulated population of neurons links to other neurons in the functional network. It is expected that this occurs because action potentials are not actually caused by the stimulation, but rather the action potentials are caused by interactions with other neurons in the network. Several aspects of the electrical stimulation in accordance with selected embodiments of the invention increase the probability of restoring neural functionality when the network is activated by a combination of electrical stimulation and favorable activities, such as rehabilitation or limb use.

Various methods in accordance with the invention can be used to treat brain damage (e.g., stroke, trauma, etc.), brain disease (e.g., Alzheimer's, Pick's, Parkinson's, etc.), brain disorders (e.g., epilepsy, depression, etc.), neurological malfunction (e.g., dyslexia, autism, etc. . . . ), and/or other neurological conditions. Various methods in accordance with the invention can also be used to enhance functions of normal, healthy brains (e.g., learning, memory, etc.), or to control sensory functions (e.g., pain).

Certain embodiments of methods in accordance with the invention electrically stimulate the brain at a stimulation site where neuroplasticity is occurring. The stimulation site may be different than the region in the brain where neural activity is typically present to perform the particular function according to the functional organization of the brain. In one embodiment in which neuroplasticity related to the neural-function occurs in the brain, the method can include identifying the location where such neuroplasticity is present. This particular procedure may accordingly enhance a change in the neural activity to assist the brain in performing the particular neural function. In an alternative embodiment in which neuroplasticity is not occurring in the brain, an aspect is to induce neuroplasticity at a stimulation site where it is expected to occur. This particular procedure may thus induce a change in the neural activity to instigate performance of the neural function. Several embodiments of these methods are expected to produce a lasting effect on the intended neural activity at the stimulation site.

The specific details of certain embodiments of the invention are set forth in the following description and in FIGS. 1A-41B to provide a thorough understanding of these embodiments to a person of ordinary skill in the art. More specifically, several embodiments of methods in accordance with the invention are initially described with reference to FIGS. 1-5E, and then several embodiments of devices for stimulating the cortical and/or deep-brain regions of the brain are described with reference to FIGS. 6-41B. A person skilled in the art will understand that the present invention may have additional embodiments, or that the invention can be practiced without several of the details described below.

A. Methods for Electrically Stimulating Regions of the Brain

1. Embodiments of Electrically Enhancing Neural Activity

Figure 1B:
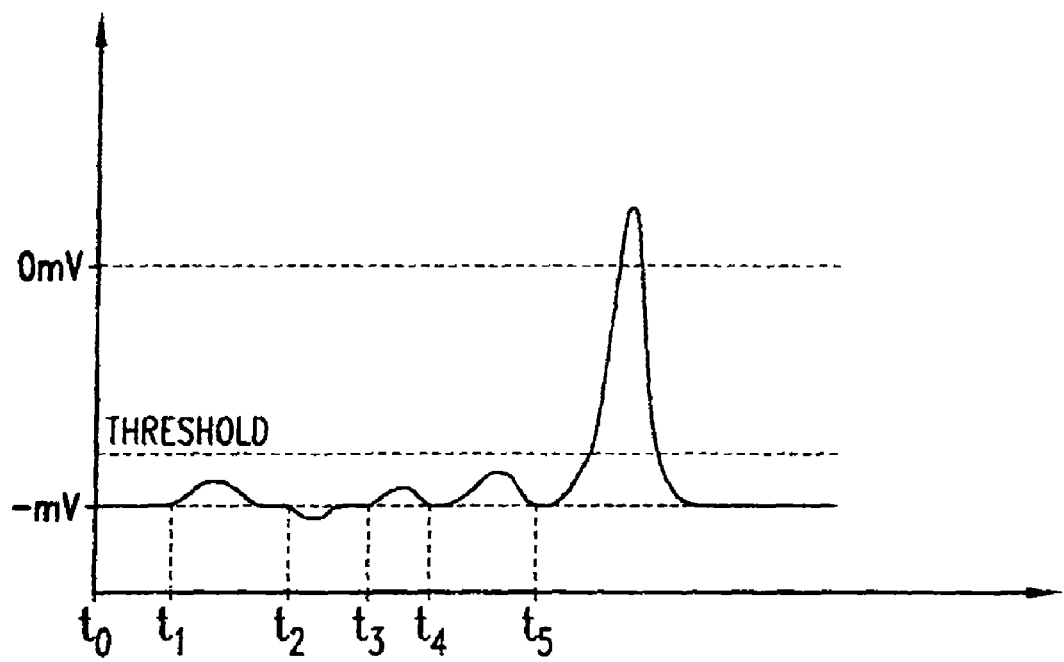
FIG. 1B is a graph illustrating firing an "action potential" associated with normal neural activity.

FIG. 1A is a schematic representation of several neurons N1-N3 and FIG. 1B is a graph illustrating an "action potential" related to neural activity in a normal neuron. Neural activity is governed by electrical impulses generated in neurons. For example, neuron N1 can send excitatory inputs to neuron N2 (e.g., times t1, t3 and t4 in FIG. 1B), and neuron N3 can send inhibitory inputs to neuron N2 (e.g., time t2 in FIG. 1B). The neurons receive/send excitatory and inhibitory inputs from/to a population of other neurons. The excitatory and inhibitory inputs can produce "action potentials" in the neurons, which are electrical pulses that travel through neurons by changing the flux of sodium (Na) and potassium (K) ions across the cell membrane. An action potential occurs when the resting membrane potential of the neuron surpasses a threshold level. When this threshold level is reached, an "all-or-nothing" action potential is generated. For example, as shown in FIG. 1B, the excitatory input at time t5 causes neuron N2 to "fire" an action potential because the input exceeds the threshold level for generating the action potential. The action potentials propagate down the length of the axon (the long process of the neuron that makes up nerves or neuronal tracts) to cause the release of neurotransmitters from that neuron that will further influence adjacent neurons.

Figure 1C:
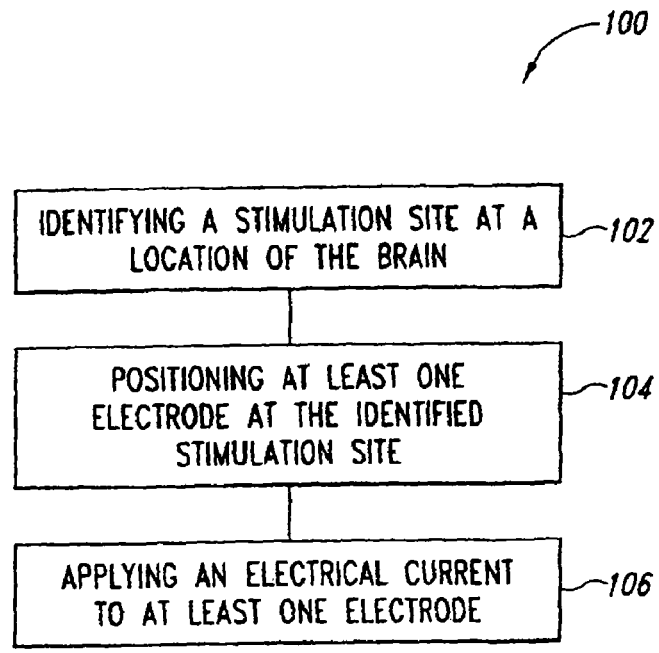
FIG. 1C is a flowchart of a method for effectuating a neural-function of a patient in accordance with one embodiment of the invention.

FIG. 1C is a flowchart illustrating a method 100 for facilitating and/or effectuating a neural-function in a patient in accordance with an embodiment of the invention. The neural-function, for example, can control a specific mental process or physiological function, such as a particular motor function (e.g., movement of a limb) or sensory function that is normally associated with neural activity at a "normal" location in the brain according to the functional organization of the brain. In several embodiments of the method 100, at least some neural activity related to the neural-function can be occurring at a site in the brain. The site of the neural activity may involve one or more portions of a normal location where neural activity typically occurs or is expected to occur to carry out the neural-function according to the functional organization of the brain, and/or the site of the neural activity may be at a different location where the brain has recruited material to perform the neural activity. In either situation, one aspect of several embodiments of the method 100 is to determine or otherwise identify the location in the brain where this neural activity is present.

The method 100 includes a diagnostic procedure 102 involving identifying a stimulation site at a location of the brain. In one approach, the stimulation site may be a location of the brain where an intended neural activity related to a given type of neural-function is present or is expected to be present. For example, the stimulation site may be particular neurological regions and/or cortical structures that are expected to direct, effectuate, and/or facilitate specific neural functions in most individuals. In another approach, the stimulation site may be a location of the brain that supports or is expected to support the intended neural-function.

The diagnostic procedure 102 may include identifying one or more exterior anatomical landmarks on the patient that correspond to such neurological regions and/or structures within the brain. The external anatomical landmarks serve as reference points for locating a structure of the brain where an intended neural activity may occur. Thus, one aspect of the diagnostic procedure 102 may include referencing the stimulation site on the brain relative to external anatomical landmarks.

More specifically, identifying an anatomical landmark may include visually determining the location of one or more reference structures (e.g., visible cranial landmarks), and locating underlying brain regions or structures (e.g., the motor strip and/or the Sylvian fissure) relative to the external location of the reference structures. Such reference structures may include, for example, the bregma, the midsagittal suture, and/or other well-known cranial landmarks in a manner understood by those skilled in the art. The methods for locating the underlying brain structure typically involve measuring distances and angles relative to the cerebral topography as known in the art of neurosurgery.

In another embodiment, the diagnostic procedure 102 includes generating an intended neural activity in the brain from a "peripheral" location that is remote from the normal location, and then determining where the intended neural activity is actually present in the brain. In an alternative embodiment, the diagnostic procedure 102 can be performed by identifying a stimulation site where neural activity has changed in response to a change in the neural-function.

The method 100 continues with an implanting procedure 104 involving positioning at least a first electrode relative to the identified stimulation site; and a stimulating procedure 106 involving applying an electrical current to the first electrode. Many embodiments of the implanting procedure 104 position two or more electrodes at the stimulation site, but other embodiments of the implanting procedure involve positioning only one electrode at the stimulation site and another electrode remotely from the stimulation site. As such, the implanting procedure 104 of the method 100 can include implanting at least one electrode at the stimulation site. Additional embodiments of the diagnostic procedure 102 and the procedures 104 and 106 are described in greater detail below.

Figure 2:
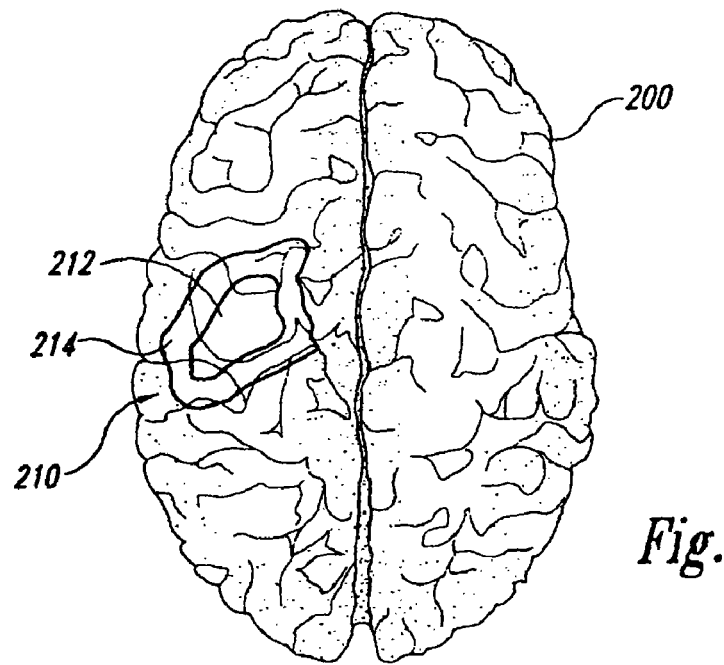
FIG. 2 is a top plan image of a portion of a brain illustrating neural activity in a first region of the brain associated with the neural-function of the patient according to the somatotopic organization of the brain.
Figure 3:
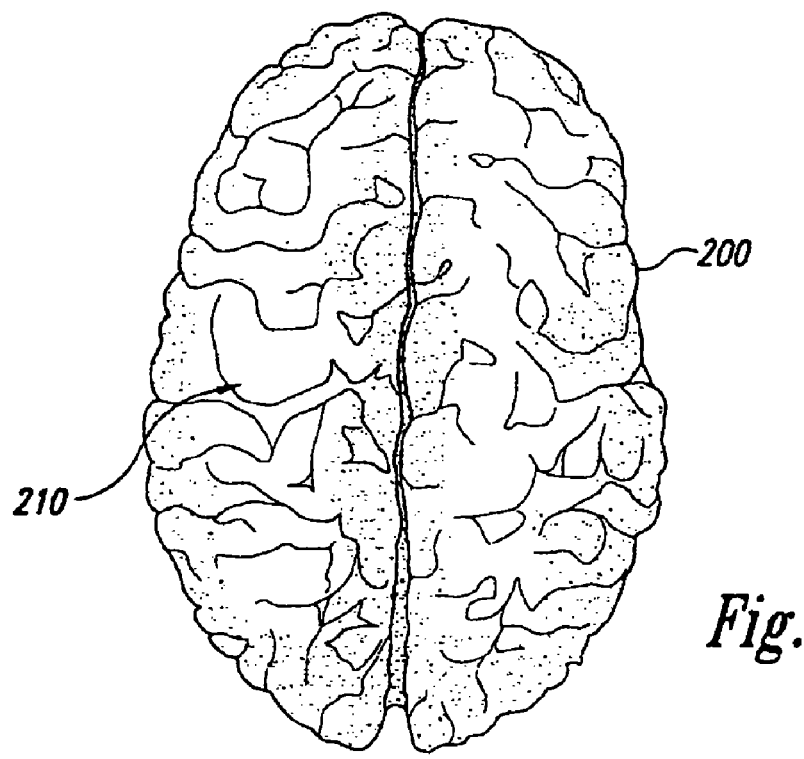
FIG. 3 is a top plan image of a portion of the brain illustrating a loss of neural activity associated with the neural-function of the patient used in one stage of a method in accordance with an embodiment of the invention.
Figure 4:
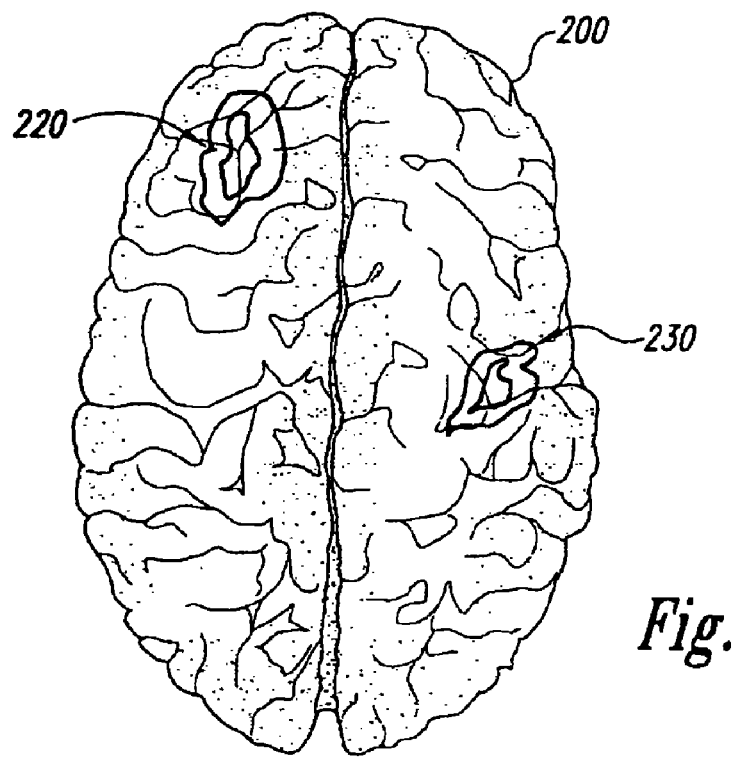
FIG. 4 is a top plan image of the brain of FIG. 3 showing a change in location of the neural activity associated with the neural-function of the patient at another stage of a method in accordance with an embodiment of the invention.

FIGS. 2-4 illustrate a specific embodiment of the diagnostic procedure 102. The diagnostic procedure 102 can be used to determine the region of the brain where stimulation will likely effectuate the desired function, such as rehabilitating a loss of a neural-function caused by a stroke, trauma, disease or other circumstance. FIG. 2, more specifically, is an image of a normal, healthy brain 200 having a first region 210 where the intended neural activity occurs to effectuate a specific neural-function in accordance with the functional organization of the brain. For example, the neural activity in the first region 210 shown in FIG. 2 is generally associated with the movement of a patient's fingers. The first region 210 can have a high-intensity area 212 and a low-intensity area 214 in which different levels of neural activity occur. It is not necessary to obtain an image of the neural activity in the first region 210 shown in FIG. 2 to carry out the diagnostic procedure 102, but rather it is provided to show an example of neural activity that typically occurs at a "normal location" according to the functional organization of the brain 200 for a large percentage of people with normal brain function. It will be appreciated that the actual location of the first region 210 will generally vary between individual patients, but those skilled in the art will recognize that the first region 210 will bear a reasonably predictable spatial relationship with respect to cranial landmarks on the patient.

The neural activity in the first region 210, however, can be impaired. In a typical application, the diagnostic procedure 102 begins by taking an image of the brain 200 that is capable of detecting neural activity to determine whether the intended neural activity associated with the particular neural function of interest is occurring at the region of the brain 200 where it normally occurs according to the functional organization of the brain. FIG. 3 is an image of the brain 200 after the first region 210 has been affected (e.g., from a stroke, trauma or other cause). As shown in FIG. 3, the neural activity that controlled the neural-function for moving the fingers no longer occurs in the first region 210. The first region 210 is thus "inactive," which is expected to result in a corresponding loss of the movement and/or sensation in the fingers. In some instances, the damage to the brain 200 may result in only a partial loss of the neural activity in the damaged region. In either case, the image shown in FIG. 3 establishes that the loss of the neural-function is related to the diminished neural activity in the first region 210. The brain 200 may accordingly recruit other neurons to perform neural activity for the affected neural-function (i.e., neuroplasticity), or the neural activity may not be present at any location in the brain.

FIG. 4 is an image of the brain 200 illustrating a plurality of potential stimulation sites 220 and 230 for effectuating the neural-function that was originally performed in the first region 210 shown in FIG. 2. FIGS. 3 and 4 show an example of neuroplasticity in which the brain compensates for a loss of neural-function in one region of the brain by recruiting other regions of the brain to perform neural activity for carrying out the affected neural-function. The diagnostic procedure 102 utilizes the neuroplasticity that occurs in the brain to identify the location of a stimulation site that is expected to be more responsive to the results of an electrical, magnetic, sonic, genetic, biologic, and/or pharmaceutical procedure to effectuate the desired neural-function.

One embodiment of the diagnostic procedure 102 involves generating the intended neural activity remotely from the first region 210 of the brain, and then detecting or sensing the location in the brain where the intended neural activity has been generated. The intended neural activity can be generated by applying an input that causes a signal to be sent to the brain. For example, in the case of a patient that has lost the use of limb, the affected limb is moved and/or stimulated while the brain is scanned using a known imaging technique that can detect neural activity (e.g., functional MRI, positron emission tomography, etc.). In one specific embodiment, the affected limb can be moved by a practitioner or the patient, stimulated by sensory tests (e.g., pricking), or subject to peripheral electrical stimulation. The movement/stimulation of the affected limb produces a peripheral neural signal from the limb that is expected to generate a response neural activity in the brain. The location in the brain where this response neural activity is present can be identified using the imaging technique. FIG. 4, for example, can be created by moving the affected fingers and then noting where neural activity occurs in response to the peripheral stimulus. By peripherally generating the intended neural activity, this embodiment may accurately identify where the brain has recruited matter (i.e., sites 220 and 230) to perform the intended neural activity associated with the neural-function.

An alternative embodiment of the diagnostic procedure 102 involves identifying a stimulation site at a second location of the brain where the neural activity has changed in response to a change in the neural-function of the patient. This embodiment of the method does not necessarily require that the intended neural activity be generated by peripherally actuating or stimulating a body part. For example, the brain can be scanned for neural activity associated with the impaired neural-function as a patient regains use of an affected limb or learns a task over a period of time. This embodiment, however, can also include peripherally generating the intended neural activity remotely from the brain explained above.

In still another embodiment, the diagnostic procedure 102 involves identifying a stimulation site at a location of the brain where the intended neural activity is developing to perform the neural-function. This embodiment is similar to the other embodiments of the diagnostic procedure 102, but it can be used to identify a stimulation site at (a) the normal region of the brain where the intended neural activity is expected to occur according to the functional organization of the brain and/or (b) a different region where the neural activity occurs because the brain is recruiting additional matter to perform the neural-function. This particular embodiment of the method involves monitoring neural activity at one or more locations where the neural activity occurs in response to the particular neural-function of interest. For example, to enhance the ability to learn a particular task (e.g., playing a musical instrument, memorizing, etc.), the neural activity can be monitored while a person performs the task or thinks about performing the task. The stimulation sites can be defined by the areas of the brain where the neural activity has the highest intensity, the greatest increases, and/or other parameters that indicate areas of the brain that are being used to perform the particular task.

Figure 5A:
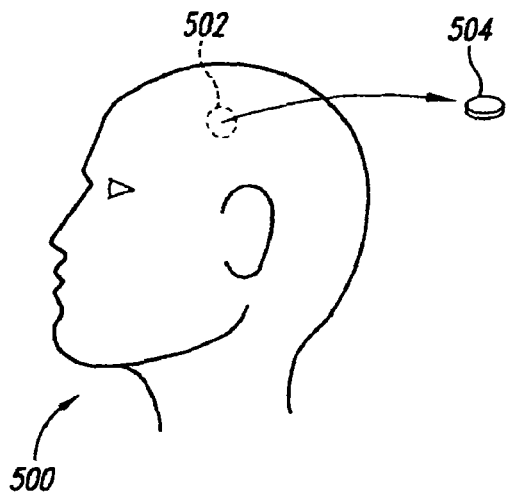
FIGS. 5A and 5B are schematic illustrations of an implanting procedure at a stage of a method in accordance with an embodiment of the invention.
Figure 5B:
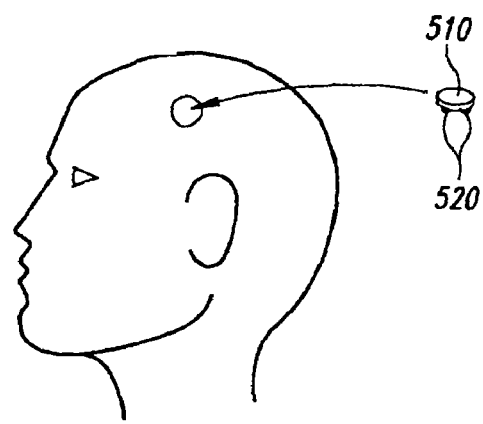

FIGS. 5A and 5B are schematic illustrations of the implanting procedure 104 described above with reference to FIG. 1C for positioning the first and second electrodes relative to a portion of the brain of a patient 500. Referring to FIG. 5A, a stimulation site 502 is identified in accordance with an embodiment of the diagnostic procedure 102. In one embodiment, a skull section 504 is removed from the patient 500 adjacent to the stimulation site 502. The skull section 504 can be removed by boring a hole in the skull in a manner known in the art, or a much smaller hole can be formed in the skull using drilling techniques that are also known in the art. In general, the hole can be 0.2-4.0 cm in diameter. Referring to FIG. 5B, an implantable stimulation apparatus 510 having first and second electrodes 520 can be implanted in the patient 500. Suitable techniques associated with the implantation procedure are known to practitioners skilled in the art. After the stimulation apparatus 510 has been implanted in the patient 500, a pulse system generates electrical pulses that are transmitted to the stimulation site 502 by the first and second electrodes 520. Stimulation apparatus suitable for carrying out the foregoing embodiments of methods in accordance with the invention are described in more detail below with reference to the FIGS. 6-40.

Several embodiments of methods for enhancing neural activity in accordance with the invention are expected to provide lasting results that promote a desired neural-function. Before the present invention, electrical and magnetic stimulation techniques typically stimulated the normal locations of the brain where neural activity related to the neural-functions occurred according to the functional organization of the brain. Such conventional techniques, however, may not by themselves be effective because one or more subpopulations of neurons in the "normal locations" of the brain may not be capable of carrying out the neural activity because of brain damage, disease, disorder, and/or because of variations of the location specific to individual patients. Several embodiments of methods for enhancing neural activity in accordance with the invention overcome this drawback by identifying a stimulation site based on neuroplastic activity that appears to be related to the neural-function. By first identifying a location in the brain that is being recruited to perform the neural activity, it is expected that therapies (e.g., electrical, magnetic, genetic, biologic, and/or pharmaceutical) applied to this location will be more effective than conventional techniques. This is because the location that the brain is recruiting for the neural activity may not be the "normal location" where the neural activity would normally occur according to the functional organization of the brain. Therefore, several embodiments of methods for enhancing neural activity in accordance with the invention are expected to provide lasting results because the therapies are applied to the portion of the brain where neural activity for carrying out the neural-function actually occurs in the particular patient.

Various embodiments of methods for enhancing neural activity in accordance with the invention may also provide lasting results because electrical stimulation therapies described herein may be applied or delivered to a patient in conjunction or simultaneous with one or more synergistic or adjunctive therapies. Such synertistic or adjunctive therapies may include or involve the patient's performance of one or more behavioral therapies, activities, and/or tasks.

2. Electrically Inducing Desired Neural Activity

The method 100 for effectuating a neural-function can also be used to induce neural activity in a region of the brain where such neural activity is not present. As opposed to the embodiments of the method 100 described above for enhancing existing neural activity, the embodiments of the method 100 for inducing neural activity initiate the neural activity at a stimulation site where it is estimated that neuroplasticity will occur. In this particular situation, an image of the brain seeking to locate where neuroplasticity is occurring may be similar to FIG. 3. An aspect of inducing neural activity, therefore, is to develop a procedure to determine where neuroplasticity is likely to occur.

A stimulation site may be identified by estimating where the brain will likely recruit neurons for performing the neural-function. In one embodiment, the location of the stimulation site is estimated by defining a region of the brain that is proximate to the normal location where neural activity related to the neural-function is generally present according to the functional organization of the brain. An alternative embodiment for locating the stimulation site includes determining where neuroplasticity has typically occurred in patients with similar symptoms. For example, if the brain typically recruits a second region of the cortex to compensate for a loss of neural activity in the normal region of the cortex, then the second region of the cortex can be selected as the stimulation site either with or without imaging the neural activity in the brain.

Several embodiments of methods for inducing neural activity in accordance with the invention are also expected to provide lasting results that initiate and promote a desired neural-function. By first estimating the location of a stimulation site where desired neuroplasticity is expected to occur, therapies applied to this location may be more effective than conventional therapies for reasons that are similar to those explained above regarding enhancing neural activity. Additionally, methods for inducing neural activity may be easier and less expensive to implement because they do not require generating neural activity and/or imaging the brain to determine where the intended neural activity is occurring before applying the therapy.

3. Applications of Methods for Electrically Stimulating Regions of the Brain

The foregoing methods for enhancing existing neural activity or inducing new neural activity are expected to be useful for many applications. As explained above, several embodiments of the method 100 involve determining an efficacious location of the brain to enhance or induce an intended neural activity that causes the desired neural-functions to occur. Additional therapies can also be implemented in combination with the electrical stimulation methods described above. Several specific applications using embodiments of electrical stimulation methods in accordance with the invention either alone or with synergistic or adjunctive therapies will now be described, but it will be appreciated that the methods in accordance with the invention can be used in many additional applications.

a. General Applications

The embodiments of the electrical stimulation methods described above are expected to be particularly useful for rehabilitating or restoring a loss of mental functions, motor functions and/or sensory functions caused by damage to the brain. In a typical application, the brain has been damaged by a stroke or trauma (e.g., automobile accident). The extent of the particular brain damage can be assessed using functional MRI or another appropriate imaging technique as explained above with respect to FIG. 3. A stimulation site can be identified in accordance with a variety of techniques, including: (a) identification of one or more anatomical landmarks; (b) peripherally stimulating a body part that was affected by the brain damage to induce the intended neural activity and determining the location where a response neural activity occurs; (c) determining where the neural activity has changed as a patient gains more use of the affected body part; (d) estimating a location that the brain may recruit neurons to carry out a type of neural activity that was previously performed by the damaged portion of the brain; and/or (e) preoperatively (for example, using TMS) and/or intraoperatively stimulating one or more brain locations to identify or map particular neural regions that induce or evoke a given type of patient response (for example, a movement or a sensation). One or more of the aforementioned techniques may be performed in conjunction or association with a neural imaging procedure. An electrical stimulation therapy can be applied to the selected stimulation site by placing or positioning the first and second electrodes relative to the stimulation site to apply an electrical current in or through that portion of the brain. As explained in more detail below, it is expected that applying an electrical current to the portion of the brain that has been recruited to perform the neural activity related to the affected body part will produce a lasting neurological effect for rehabilitating the affected body part. The extent to which electrical stimulation therapy produces a lasting neurological effect may also be related to the performance of behavioral therapy or tasks in conjunction or simultaneous with the electrical stimulation therapy.

Several specific applications are expected to have a stimulation site in the cortex because neural activity in this part of the brain effectuates motor functions and/or sensory functions that are typically affected by a stroke or trauma. In these applications, the electrical stimulation can be applied directly to the pial surface of the brain or at least proximate to the pial surface (e.g., the dura mater, the fluid surrounding the cortex, or neurons within the cortex). Suitable devices for applying the electrical stimulation to the cortex are described in detail with reference to FIGS. 6-41B.

Figure 5E:
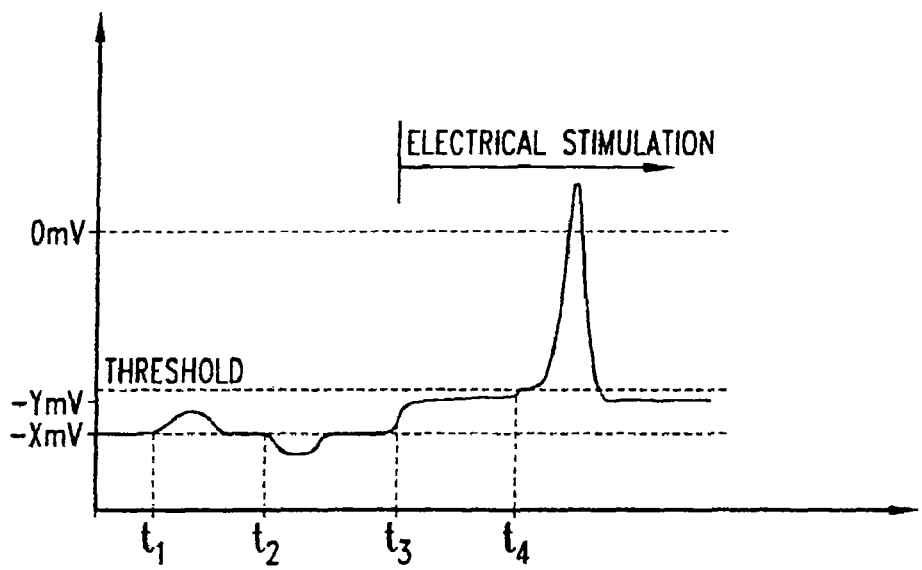
FIG. 5E is a graph illustrating firing an "action potential" associated with stimulated neural activity in accordance with one embodiment of the invention.
Figure 5C:
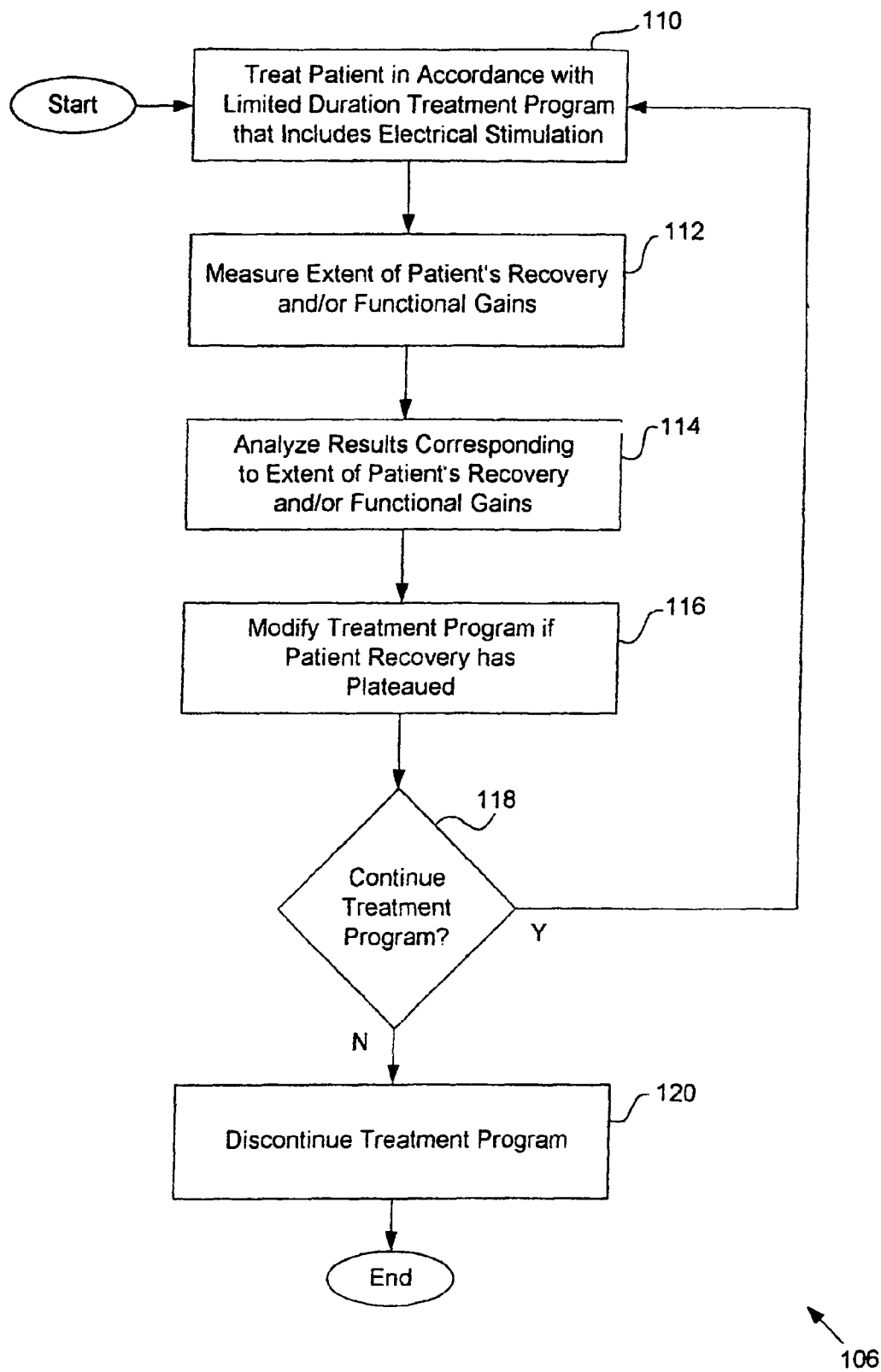
FIGS. 5C and 5D are flowcharts of stimulation procedures for applying electrical stimulation to a region of a patient's brain.

FIG. 5C is a flowchart of an embodiment of a stimulating procedure 106 described above with reference to FIG. 1C for applying electrical stimulation to a region of a patient's brain identified in accordance with an associated diagnostic procedure 102. In one embodiment, the stimulating procedure 106 includes a limited duration treatment program 110 involving the application of electrical stimulation to the patient in a manner that facilitates or effectuates complete, essentially complete, significant, or partial rehabilitation, restoration, or functional healing of or recovery from a neurological condition such as a neurological malfunction and/or a neurologically based deficit or disorder. One or more portions of the treatment program 110 may involve electrical stimulation by itself, and/or electrical stimulation in conjunction with one or more synergistic or adjunctive therapies, such as behavioral therapies, activities, and/or tasks. Such behavioral therapies, activities, and/or tasks may include physical therapy; physical and/or cognitive skills training or practice, such as training in Activities of Daily Living (ADL); intentional use of an affected body part; speech therapy; vision training or visual tasks; a reading task; a memory task or memory training; comprehension tasks; attention tasks; and/or other therapies or activities. Other synergistic or adjunctive therapies may include, for example, drug therapies, such as treatment with amphetamines. The electrical stimulation and synergistic or adjunctive therapies can be performed simultaneously or serially.

In accordance with the present invention, a limited duration treatment program 110 may effectuate or facilitate at least some degree of permanent, essentially permanent, or long term rehabilitation or restoration of a patient's ability to perform one or more types of physical and/or cognitive functions that had been lost or degraded due to neurological damage or a neurological disorder. A limited duration treatment program 110 may alternatively or additionally effectuate or facilitate at least some degree of permanent, essentially permanent, or long term development, acquisition, and/or establishment of a patient's ability to perform one or more types of physical and/or cognitive functions that had been at least partially absent or impaired as a result of a neurological malfunction. Therefore, the treatment program 110 need not be directed toward managing a chronic condition that exists over a very long period of time or throughout a patient's life. Rather, the treatment program 110 may be applied over a limited time that corresponds to the extent of the patient's recovery or functional gain(s). For example, the treatment program 110 may occur over a period of six weeks, three months, six months, one year, three years, or another limited timeframe. Alternatively or additionally, the treatment program 110 may be applied over a predetermined number of treatment sessions, for example, twenty, thirty, fifty, or some other number of treatment sessions in total. Another aspect may limit the duration of the treatment program to an accumulated or aggregate time that stimulation has been applied over some number of treatment sessions. An exemplary treatment program 110 may include one to four or more hours of electrical stimulation per stimulation session, three to seven stimulation sessions per week, throughout a therapy period of one to six or more weeks. Alternatively, a treatment program 110 may apply continuous or essentially continuous neural stimulation during one or more portions of a therapy period. The overall length or duration of the treatment program 110 (i.e., the therapy period), and possibly the type(s) and/or location(s) of applied neural stimulation, may depend upon the nature, number, and/or severity of the patient's functional deficits, as well as a degree of patient recovery or functional development.

The stimulating procedure 106 may further include an assessing procedure 112 for determining the extent of the patient's functional rehabilitation, recovery, and/or development at particular intervals or over time. Such intervals may be, for example, every n weeks, or every kth treatment session. The assessing procedure 112 may involve rating or measuring the patient's physical and/or cognitive abilities in accordance with one or more standard functional measures or tests. Such functional measures may include or be based upon, for example, a Fugl-Meyer Assessment of Sensorimotor Impairment; a National Institute of Health (NIH) Stroke Scale; a Stroke Impact Scale (SIS); an ADL scale; a Quality of Life (QoL) scale; physical measures such as grip strength or finger tapping speed; a neuropsychological testing battery; a walking, movement, and/or dexterity test; a behavioral test; a language test; a comprehension test; and/or other measures of patient functional ability. The assessing procedure 112 may additionally or alternatively include one or more neural imaging procedures. The assessing procedure 112 can also be used to determine the severity of the patient's functional deficits or other neurological conditions at the beginning and throughout the therapy period.

In one embodiment, the stimulating procedure 106 may include an analyzing procedure 114 for examining results obtained from one or more assessing procedures 112. The analyzing procedure 114 may involve data analysis and/or trend analysis techniques. In the event that the patient's functional development and/or recovery has significantly slowed or plateaued, but further recovery may be likely or possible, the stimulating procedure 106 may include a modification procedure 116 for changing, adjusting, or adapting the limited duration treatment program 110. The treatment program 110 may be changed, adjusted, or adapted by varying stimulation type(s), stimulation location(s), stimulation parameters, and/or particular synergistic or adjunctive therapies (e.g., behavioral therapies, activities, and/or tasks).

The stimulating procedure 106 may further include a determining procedure 118 for deciding whether to continue a treatment program 110. In the event that a treatment program 110 is not yet complete or has been modified or adjusted, the treatment program 110 may resume or restart. In the event that the patient has functionally developed and/or recovered to an intended, acceptable, or maximum extent, the stimulating procedure 106 may include a termination procedure 120 for discontinuing the treatment program 110. After the treatment program 110 is completed or discontinued, the patient's functional recovery or gains in functional ability may persist or be retained on a permanent, essentially permanent, or long term basis without further electrical stimulation therapy.

Figure 5D:
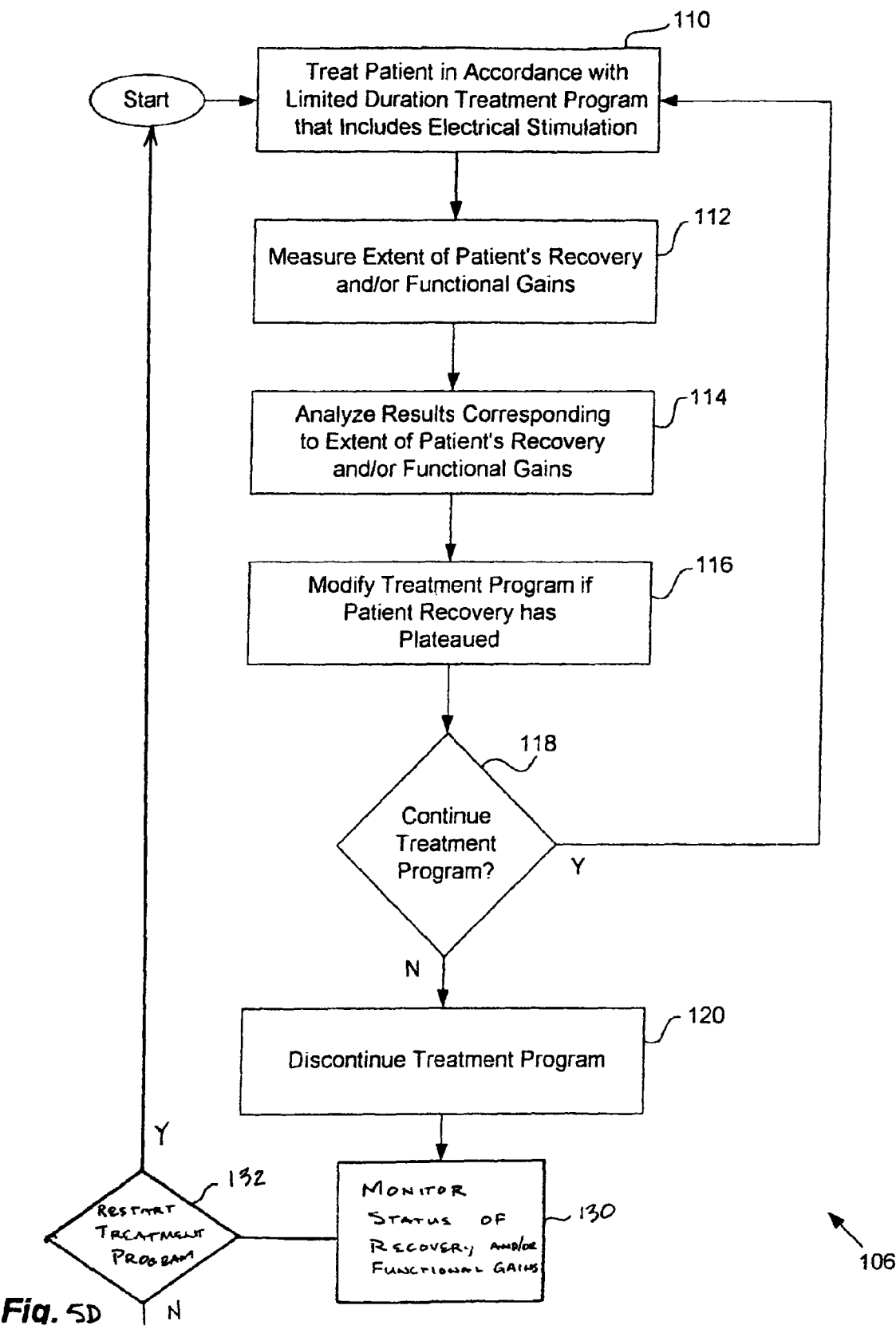

FIG. 5D is a flow chart of another embodiment of a stimulating procedure 106 described above with reference to FIG. 1C for applying electrical stimulation to a region of a patient's brain identified in accordance with an associated diagnostic procedure 102. The embodiment of the stimulating procedure 106 shown in FIG. 5D is similar to the procedure shown in FIG. 5C. The stimulating procedure 106 show in FIG. 5D, however, further includes a monitoring operation 130 in which the status of the recovery and/or functional gains is monitored after a period of time to determine whether they have been retained on a permanent or long-term basis without further electrical stimulation therapy. In many applications it is anticipated that the treatment program of procedures 110-120 over a limited therapy period will be sufficient to retain the recovery or gains in functional ability on a permanent, essentially permanent or long-term basis without further electrical stimulation therapy. The procedure 106 shown in FIG. 5D, however, is applicable in situations that require further treatment. The stimulation procedure 106 in FIG. 5D accordingly further includes a second determining procedure 132 for deciding whether to restart the treatment program. If the results from the monitoring operation 130 indicate that the patient has retained an intended, acceptable or maximum recovery in and/or development of a functional ability, then the determining procedure 132 may proceed to terminate the treatment program. On the other hand, if the monitoring operation 130 establishes that the recovery in and/or development of functional ability has not been retained or can be further improved, then the determining procedure 132 restarts the treatment program 110. It will be appreciated that this process can include a number of different iterations.

Various embodiments of the electrical stimulation methods described above may be useful for treating brain diseases, such as Alzheimer's, Parkinson's, and other brain diseases. In this application, a stimulation site can be identified by monitoring the neural activity using functional MRI or other suitable imaging techniques over a period of time to determine where the brain is recruiting material to perform the neural activity that is being affected by the disease. It may also be possible to identify a stimulation site by having the patient try to perform an act that the particular disease has affected, and monitoring the brain to determine whether any response neural activity is present in the brain. After identifying where the brain is recruiting additional matter, the electrical stimulation can be applied to this portion of the brain. It is expected that electrically stimulating the regions of the brain that have been recruited to perform the neural activity which was affected by the disease will assist the brain in offsetting the damage caused by the disease.

Various embodiments of the electrical stimulation methods described above are also expected to be useful for treating neurological disorders, such as depression, passive-aggressive behavior, weight control, and other disorders. In these applications, the electrical stimulation can be applied to a stimulation site in the cortex or another suitable part of the brain where neural activity related to the particular disorder is present. The embodiments of electrical stimulation methods for carrying out the particular therapy can be adapted to either increase or decrease the particular neural activity in a manner that produces the desired results. For example, an amputee may feel phantom sensations associated with the amputated limb. This phenomenon can be treated by applying an electrical pulse that reduces the phantom sensations. The electrical therapy can be applied so that it will modulate the ability of the neurons in that portion of the brain to execute sensory functions.

b. Pulse Forms and Potentials

The electrical stimulation methods in accordance with the invention can use several different pulse forms to effectuate the desired neuroplasticity. The pulses can be a bi-phasic or monophasic stimulus that is applied to achieve a desired potential in a sufficient percentage of a population of neurons at the stimulation site. In one embodiment, the pulse form has a frequency of approximately 2-1000 Hz, but the frequency may be particularly useful in the range of approximately 40-200 Hz. For example, initial clinical trials are expected to use a frequency of approximately 50-100 Hz. The pulses can also have pulse widths of approximately 10 μs-100 ms, or more specifically the pulse width can be approximately 20-200 μs. For example, a pulse width of 50-100 μs may produce beneficial results.

It is expected that one particularly useful application of the invention involves enhancing or inducing neuroplasticity by raising the resting membrane potential of neurons to bring the neurons closer to the threshold level for firing an action potential. Because the stimulation raises the resting membrane potential of the neurons, it is expected that these neurons are more likely to "fire" an action potential in response to excitatory input at a lower level.

FIG. 5E is a graph illustrating applying a subthreshold potential to the neurons N1-N3 of FIG. 1A. At times t1 and t2, the excitory/inhibitory inputs from other neurons do not "bridge-the-gap" from the resting potential at $-X$ mV to the threshold potential. At time t3, the electrical stimulation is applied to the brain to raise the resting potential of neurons in the stimulated population such that the resting potential is at $-Y$ mV. As such, at time t4 when the neurons receive another excitatory input, even a small input exceeds the gap between the raised resting potential $-Y$ mV and the threshold potential to induce action potentials in these neurons. For example, if the resting potential is approximately $-70$ mV and the threshold potential is approximately $-50$ mV, then the electrical stimulation can be applied to raise the resting potential of a sufficient number of neurons to approximately $-52$ to $-60$ mV.

The actual electrical potential applied to electrodes implanted in the brain to achieve a subthreshold potential stimulation will vary according to the individual patient, the type of therapy, the type of electrodes, and other factors. In general, the pulse form of the electrical stimulation (e.g., the frequency, pulse width, wave form, and voltage potential) is selected to raise the resting potential in a sufficient number neurons at the stimulation site to a level that is less than a threshold potential for a statistical portion of the neurons in the population. The pulse form, for example, can be selected so that the applied voltage of the stimulus achieves a change in the resting potential of approximately 10%-95%, and more specifically of 60%-80%, of the difference between the unstimulated resting potential and the threshold potential.

In one specific example of a subthreshold application for treating a patient's hand, electrical stimulation is not initially applied to the stimulation site. Although physical therapy related to the patient's hand may cause some activation of a particular population of neurons that is known to be involved in "hand function," only a low level of activation might occur because physical therapy only produces a low level of action potential generation in that population of neurons. However, when the subthreshold electrical stimulation is applied, the resting membrane potentials of the neurons in the stimulated population are elevated. These neurons now are much closer to the threshold for action potential formation such that when the same type of physical therapy is given, this population of cells will have a higher level of activation because these cells are more likely to fire action potentials.

Subthreshold stimulation may produce better results than simply stimulating the neurons with sufficient energy levels to exceed the threshold for action potential formation. One aspect of subthreshold stimulation is to increase the probability that action potentials will occur in response to the ordinary causes of activation—such as physical therapy. This will allow the neurons in this functional network to become entrained together, or "learn" to become associated with these types of activities. If neurons are given so much electricity that they continually fire action potentials without additional excitatory inputs (suprathreshold stimulation), this will create "noise" and disorganization that will not likely cause improvement in function. In fact, neurons that are "over-driven" soon deplete their neurotransmitters and effectively become silent.

The application of a subthreshold stimulation is very different than suprathreshold stimulation. Subthreshold stimulation in accordance with several embodiments of the invention, for example, does not intend to directly make neurons fire action potentials with the electrical stimulation in a significant population of neurons at the stimulation site. Instead, subthreshold stimulation attempts to decrease the "activation energy" required to activate a large portion of the neurons at the stimulation site. As such, subthreshold stimulation in accordance with certain embodiments of the invention is expected to increase the probability that the neurons will fire in response to the usual intrinsic triggers, such as trying to move a limb, physical therapy, or simply thinking about movement of a limb, etc. Moreover, coincident stimulation associated with physical therapy is expected to increase the probability that the action potentials that are occurring with an increased probability due to the subthreshold stimulation will be related to meaningful triggers, and not just "noise."

The stimulus parameters set forth above, such as a frequency selection of approximately 50-100 Hz and an amplitude sufficient to achieve an increase of 60% to 80% of the difference between the resting potential and the threshold potential are specifically selected so that they will increase the resting membrane potential of the neurons, thereby increasing the likelihood that they will fire action potentials, without directly causing action potentials in most of the neuron population. In addition, and as explained in more detail below with respect to FIGS. 6-40, several embodiments of stimulation apparatus in accordance with the invention are designed to precisely apply a pulse form that produces subthreshold stimulation by selectively stimulating regions of the cerebral cortex of approximately 1-2 cm (the estimated size of a "functional unit" of cortex), directly contacting the pial surface with the electrodes to consistently create the same alterations in resting membrane potential, and/or biasing the electrodes against the pial surface to provide a positive connection between the electrodes and the cortex.

B. Devices for Electrically Stimulating Regions of the Brain

FIGS. 6-40 illustrate stimulation apparatus in accordance with several embodiments of the invention for electrically stimulating regions of the brain in accordance with one or more of the methods described above. The devices illustrated in FIGS. 6-40 are generally used to stimulate a region of the cortex proximate to the pial surface of the brain (e.g., the dura mater, the pia mater, the fluid between the dura mater and the pia mater, and a depth in the cortex outside of the white matter of the brain). The devices can also be adapted for stimulating other portions of the brain in other embodiments.

1. Implantable Stimulation Apparatus with Integrated Pulse Systems

Figure 6:
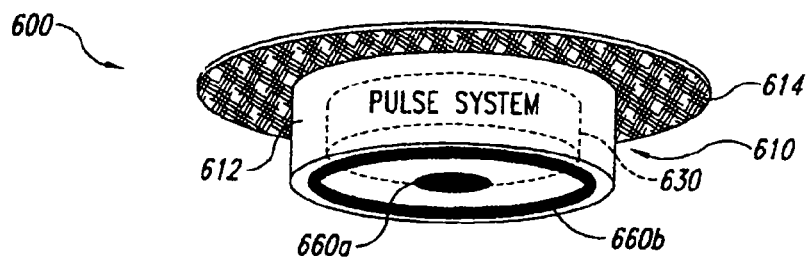
FIG. 6 is an isometric view of an implantable stimulation apparatus in accordance with one embodiment of the invention.
Figure 7:
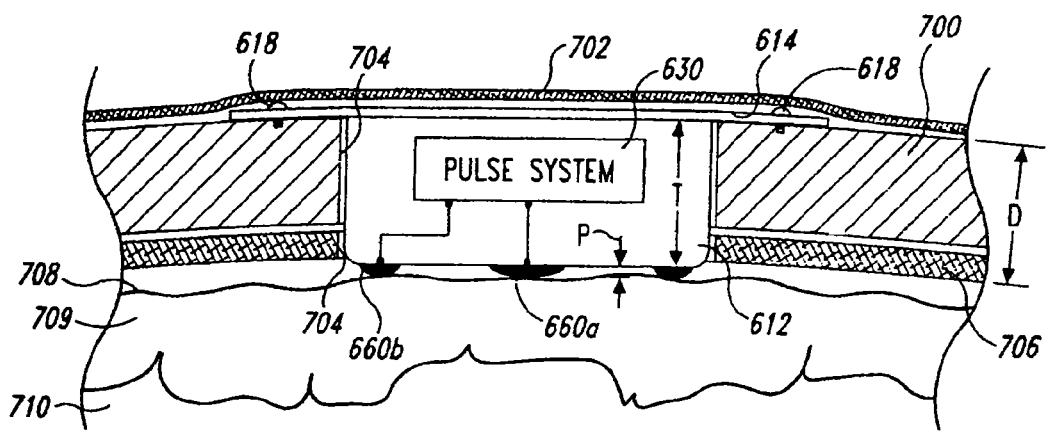
FIG. 7 is a cross-sectional view schematically illustrating a part of an implantable stimulation apparatus in accordance with an embodiment of the invention.

FIG. 6 is an isometric view and FIG. 7 is a cross-sectional view of a stimulation apparatus 600 in accordance with an embodiment of the invention for stimulating a region of the cortex proximate to the pial surface. In one embodiment, the stimulation apparatus 600 includes a support member 610, an integrated pulse-system 630 (shown schematically) carried by the support member 610, and first and second electrodes 660 (identified individually by reference numbers 660a and 660b). The first and second electrodes 660 are electrically coupled to the pulse system 630. The support member 610 can be configured to be implanted into the skull or another intracranial region of a patient. In one embodiment, for example, the support member 610 includes a housing 612 and an attachment element 614 connected to the housing 612. The housing 612 can be a molded casing formed from a biocompatible material that has an interior cavity for carrying the pulse system 630. The housing can alternatively be a biocompatible metal or another suitable material. The housing 612 can have a diameter of approximately 1-4 cm, and in many applications the housing 612 can be 1.5-2.5 cm in diameter. The housing 612 can also have other shapes (e.g., rectilinear, oval, elliptical) and other surface dimensions. The stimulation apparatus 600 can weigh 35 g or less and/or occupy a volume of 20 cc or less. The attachment element 614 can be a flexible cover, a rigid plate, a contoured cap, or another suitable element for holding the support member 610 relative to the skull or other body part of the patient. In one embodiment, the attachment element 614 is a mesh, such as a biocompatible polymeric mesh, metal mesh, or other suitable woven material. The attachment element 614 can alternatively be a flexible sheet of Mylar, a polyester, or another suitable material.

FIG. 7, more specifically, is a cross-sectional view of the stimulation apparatus 600 after it has been implanted into a patient in accordance with an embodiment of the invention. In this particular embodiment, the stimulation apparatus 600 is implanted into the patient by forming an opening in the scalp 702 and cutting a hole 704 through the skull 700 and through the dura mater 706. The hole 704 should be sized to receive the housing 612 of the support member 610, and in most applications, the hole 704 should be smaller than the attachment element 614. A practitioner inserts the support member 610 into the hole 704 and then secures the attachment element 614 to the skull 700. The attachment element 614 can be secured to the skull using a plurality of fasteners 618 (e.g., screws, spikes, etc.) or an adhesive. In an alternative embodiment, a plurality of downwardly depending spikes can be formed integrally with the attachment element 614 to define anchors that can be driven into the skull 700.

The embodiment of the stimulation apparatus 600 shown in FIG. 7 is configured to be implanted into a patient so that the electrodes 660 contact a desired portion of the brain at the stimulation site. The housing 612 and the electrodes 660 can project from the attachment element 614 by a distance "D" such that the electrodes 660 are positioned at least proximate to the pia mater 708 surrounding the cortex 709. The electrodes 660 can project from a housing 612 as shown in FIG. 7, or the electrodes 660 can be flush with the interior surface of the housing 612. In the particular embodiment shown in FIG. 7, the housing 612 has a thickness "T" and the electrodes 660 project from the housing 612 by a distance "P" so that the electrodes 660 press against the surface of the pia mater 708. The thickness of the housing 612 can be approximately 0.5-4 cm, and is more generally about 1-2 cm. The configuration of the stimulation apparatus 600 is not limited to the embodiment shown in FIGS. 6 and 7, but rather the housing 612, the attachment element 614, and the electrodes 660 can be configured to position the electrodes in several different regions of the brain. For example, in an alternate embodiment, the housing 612 and the electrodes 660 can be configured to position the electrodes deep within the cortex 709, and/or a deep brain region 710. In general, the electrodes can be flush with the housing or extend 0.1 mm to 5 cm from the housing. More specific embodiments of pulse system and electrode configurations for the stimulation apparatus will be described below.

Several embodiments of the stimulation apparatus 600 are expected to be more effective than existing transcranial electrical stimulation devices and transcranial magnetic stimulation devices. It will be appreciated that much of the power required for transcranial therapies is dissipated in the scalp and skull before it reaches the brain. In contrast to conventional transcranial stimulation devices, the stimulation apparatus 600 is implanted so that the electrodes are at least proximate to the pial surface of the brain 708. Several embodiments of methods in accordance with the invention can use the stimulation apparatus 600 to apply an electrical therapy directly to the pia mater 708, the dura mater 706, and/or another portion of the cortex 709 at significantly lower power levels than existing transcranial therapies. For example, a potential of approximately 1 mV to 10 V can be applied to the electrodes 660; in many instances a potential of 100 mV to 5 V can be applied to the electrodes 660 for selected applications. It will also be appreciated that other potentials can be applied to the electrodes 660 of the stimulation apparatus 600 in accordance with other embodiments of the invention.

Selected embodiments of the stimulation apparatus 600 are also capable of applying stimulation to a precise stimulation site. Again, because the stimulation apparatus 600 positions the electrodes 660 at least proximate to the pial surface 708, precise levels of stimulation with good pulse shape fidelity will be accurately transmitted to the stimulation site in the brain. It will be appreciated that transcranial therapies may not be able to apply stimulation to a precise stimulation site because the magnetic and electrical properties of the scalp and skull may vary from one patient to another such that an identical stimulation by the transcranial device may produce a different level of stimulation at the neurons in each patient. Moreover, the ability to focus the stimulation to a precise area is hindered by delivering the stimulation transcranially because the scalp, skull and dura all diffuse the energy from a transcranial device. Several embodiments of the stimulation apparatus 600 overcome this drawback because the electrodes 660 are positioned under the skull 700 such that the pulses generated by the stimulation apparatus 600 are not diffused by the scalp 702 and skull 700.

2. Integrated Pulse Systems for Implantable Stimulation Apparatus

The pulse system 630 shown in FIGS. 6 and 7 generates and/or transmits electrical pulses to the electrodes 660 to create an electrical field at a stimulation site in a region of the brain. The particular embodiment of the pulse system 630 shown in FIG. 7 is an "integrated" unit in that is carried by the support member 610. The pulse system 630, for example, can be housed within the housing 612 so that the electrodes 660 can be connected directly to the pulse system 630 without having leads outside of the stimulation apparatus 600. The distance between the electrodes 660 and the pulse system 630 can be less than 4 cm, and it is generally 0.10 to 2.0 cm. The stimulation apparatus 600 can accordingly provide electrical pulses to the stimulation site without having to surgically create tunnels running through the patient to connect the electrodes 660 to a pulse generator implanted remotely from the stimulation apparatus 600. It will be appreciated, however, that alternative embodiments of stimulation apparatus in accordance with the invention can include a pulse system implanted separately from the stimulation apparatus 600 in the cranium or an external pulse system. Several particular embodiments of pulse systems that are suitable for use with the stimulation apparatus 600 will now be described in more detail.

Figure 8:
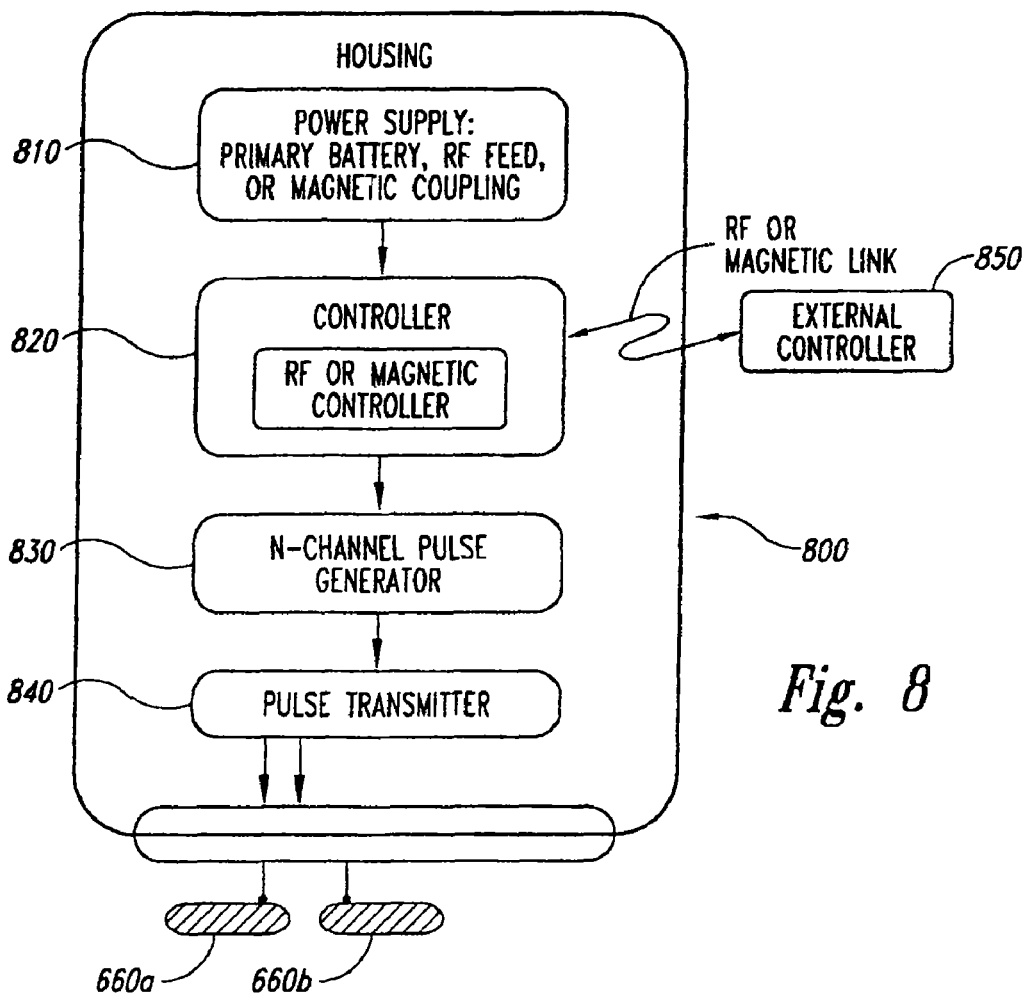
FIG. 8 is a schematic illustration of a pulse system in accordance with one embodiment of the invention.
Figure 9:
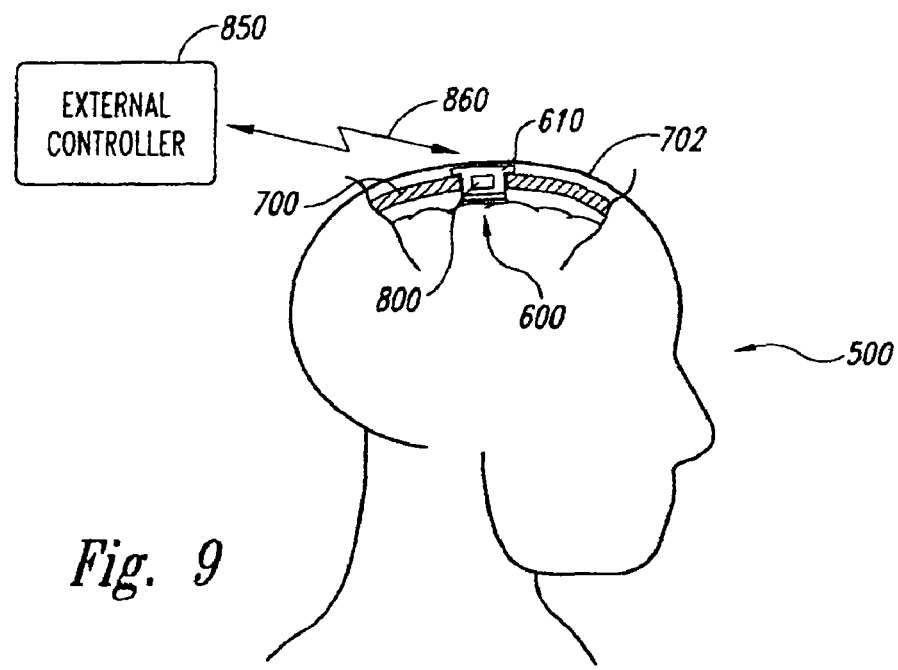
FIG. 9 is a schematic illustration of an implanted stimulation apparatus and an external controller in accordance with an embodiment of the invention.

FIGS. 8 and 9 schematically illustrate an integrated pulse system 800 in accordance with one embodiment of the invention for being implanted in the cranium within the stimulation apparatus 600. Referring to FIG. 8, the pulse system 800 can include a power supply 810, an integrated controller 820, a pulse generator 830, and a pulse transmitter 840. The power supply 810 can be a primary battery, such as a rechargeable battery or another suitable device for storing electrical energy. In alternative embodiments, the power supply 810 can be an RF transducer or a magnetic transducer that receives broadcast energy emitted from an external power source and converts the broadcast energy into power for the electrical components of the pulse system 800. The integrated controller 820 can be a wireless device that responds to command signals sent by an external controller 850. The integrated controller 820, for example, can communicate with the external controller 850 by RF or magnetic links 860. The integrated controller 820 provides control signals to the pulse generator 830 in response to the command signals sent by the external controller 850. The pulse generator 830 can have a plurality of channels that send appropriate electrical pulses to the pulse transmitter 840, which is coupled to the electrodes 660. Suitable components for the power supply 810, the integrated controller 820, the pulse generator 830, and the pulse transmitter 840 are known to persons skilled in the art of implantable medical devices.

Referring to FIG. 9, the pulse system 800 can be carried by the support member 610 of the stimulation apparatus 600 in the manner described above with reference to FIGS. 6 and 7. The external controller 850 can be located externally to the patient 500 so that the external controller 850 can be used to control the pulse system 800. In one embodiment, several patients that require a common treatment can be simultaneously treated using a single external controller 850 by positioning the patients within the operating proximity of the controller 850. In an alternative embodiment, the external controller 850 can contain a plurality of operating codes and the integrated controller 820 for a particular patient can have an individual operating code. A single controller 850 can thus be used to treat a plurality of different patients by entering the appropriate operating code into the controller 850 corresponding to the particular operating codes of the integrated controllers 820 for the patients.

Figure 10:
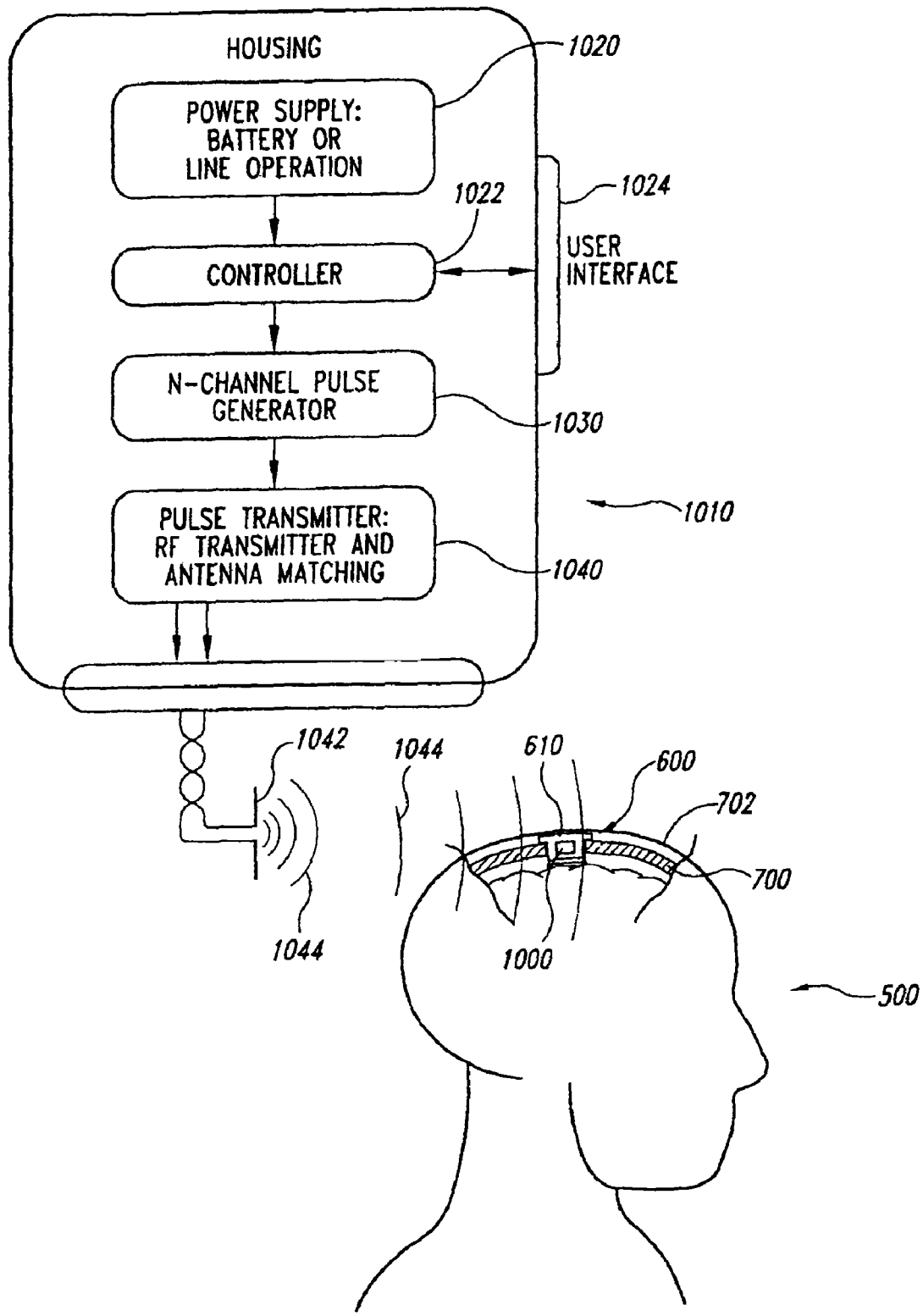
FIG. 10 is a schematic illustration of an implantable stimulation apparatus having a pulse system and an external controller in accordance with another embodiment of the invention.

FIG. 10 is a schematic view illustrating a pulse system 1000 and an external controller 1010 for use with the stimulation apparatus 600 in accordance with another embodiment of the invention. In this embodiment, the external controller 1010 includes a power supply 1020, a controller 1022 coupled to the power supply 1020, and a user interface 1024 coupled to the controller 1022. The external controller 1010 can also include a pulse generator 1030 coupled to the power supply 1020, a pulse transmitter 1040 coupled to the pulse generator 1030, and an antenna 1042 coupled to the pulse transmitter 1040. The external controller 1010 generates the power and the pulse signal, and the antenna 1042 transmits a pulse signal 1044 to the pulse system 1000 in the stimulation apparatus 600. The pulse system 1000 receives the pulse signal 1044 and delivers an electrical pulse to the electrodes. The pulse system 1000, therefore, does not necessarily include an integrated power supply, controller and pulse generator within the housing 610 because these components are in the external controller 1010.

Figure 11:
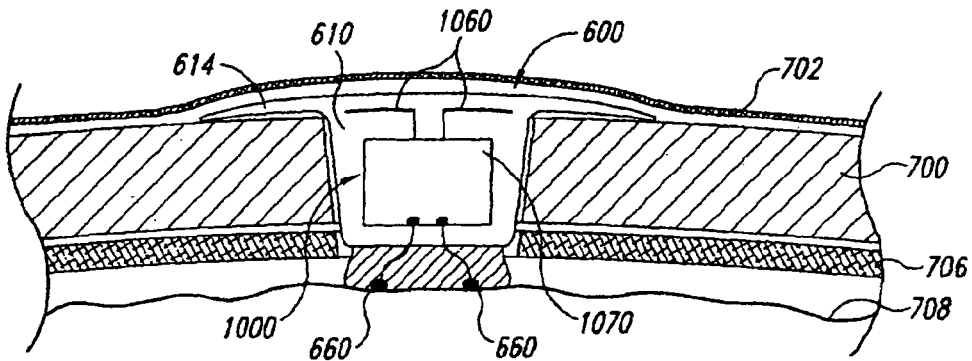
FIG. 11 is a cross-sectional view schematically illustrating a part of an implantable stimulation apparatus in accordance with an embodiment of the invention.

FIG. 11 is a schematic view illustrating an embodiment of the pulse system 1000 in greater detail. In this embodiment, the pulse system 1000 is carried by the support member 610 of the stimulation apparatus 600. The pulse system 1000 can include an antenna 1060 and a pulse delivery system 1070 coupled to the antenna 1060. The antenna 1060 receives the pulse signal 1044 from the external controller 1010 and sends the pulse signal 1044 to the pulse delivery system 1070, which transforms the pulse signal 1044 into electrical pulses. Accordingly, the electrodes 660 can be coupled to the pulse delivery system 1070. The pulse delivery system 1070 can include a filter to remove noise from the pulse signal 1044 and a pulse former that creates an electrical pulse from the pulse signal 1044. The pulse former can be driven by the energy in the pulse signal 1044, or in an alternative embodiment, the pulse system 1000 can also include an integrated power supply to drive the pulse former.

Figure 12:
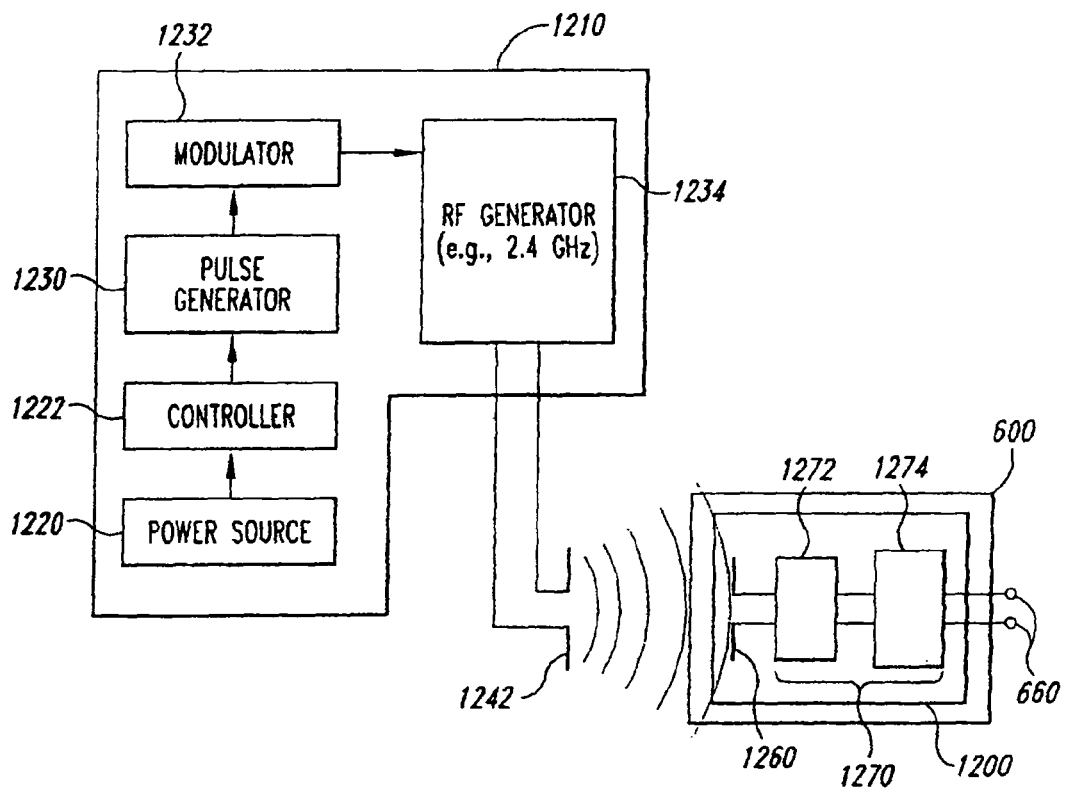
FIG. 12 is a schematic illustration of an implantable stimulation apparatus having a pulse system and an external controller in accordance with another embodiment of the invention.

FIG. 12 is a schematic view illustrating an embodiment of pulse system 1200 for use in an embodiment of the stimulation apparatus 600, and an external controller 1210 for controlling the pulse system 1200 remotely from the patient using RF energy. In this embodiment, the external controller 1210 includes a power supply 1220, a controller 1222 coupled to the power supply 1220, and a pulse generator 1230 coupled to the controller 1222. The external controller 1210 can also include a modulator 1232 coupled to the pulse generator 1230 and an RF generator 1234 coupled to the modulator 1232. In operation, the external controller 1210 broadcasts pulses of RF energy via an antenna 1242.

The pulse system 1200 can be housed within the stimulation apparatus 600 (not shown). In one embodiment, the pulse system 1200 includes an antenna 1260 and a pulse delivery system 1270. The antenna 1260 incorporates a diode (not shown) that rectifies the broadcast RF energy from the antenna 1242. The pulse delivery system 1270 can include a filter 1272 and a pulse former 1274 that forms electrical pulses which correspond to the RF energy broadcast from the antenna 1242. The pulse system 1200 is accordingly powered by the RF energy in the pulse signal from the external controller 1210 such that the pulse system 1200 does not need a separate power supply carried by the stimulation apparatus 600.

Figure 13:
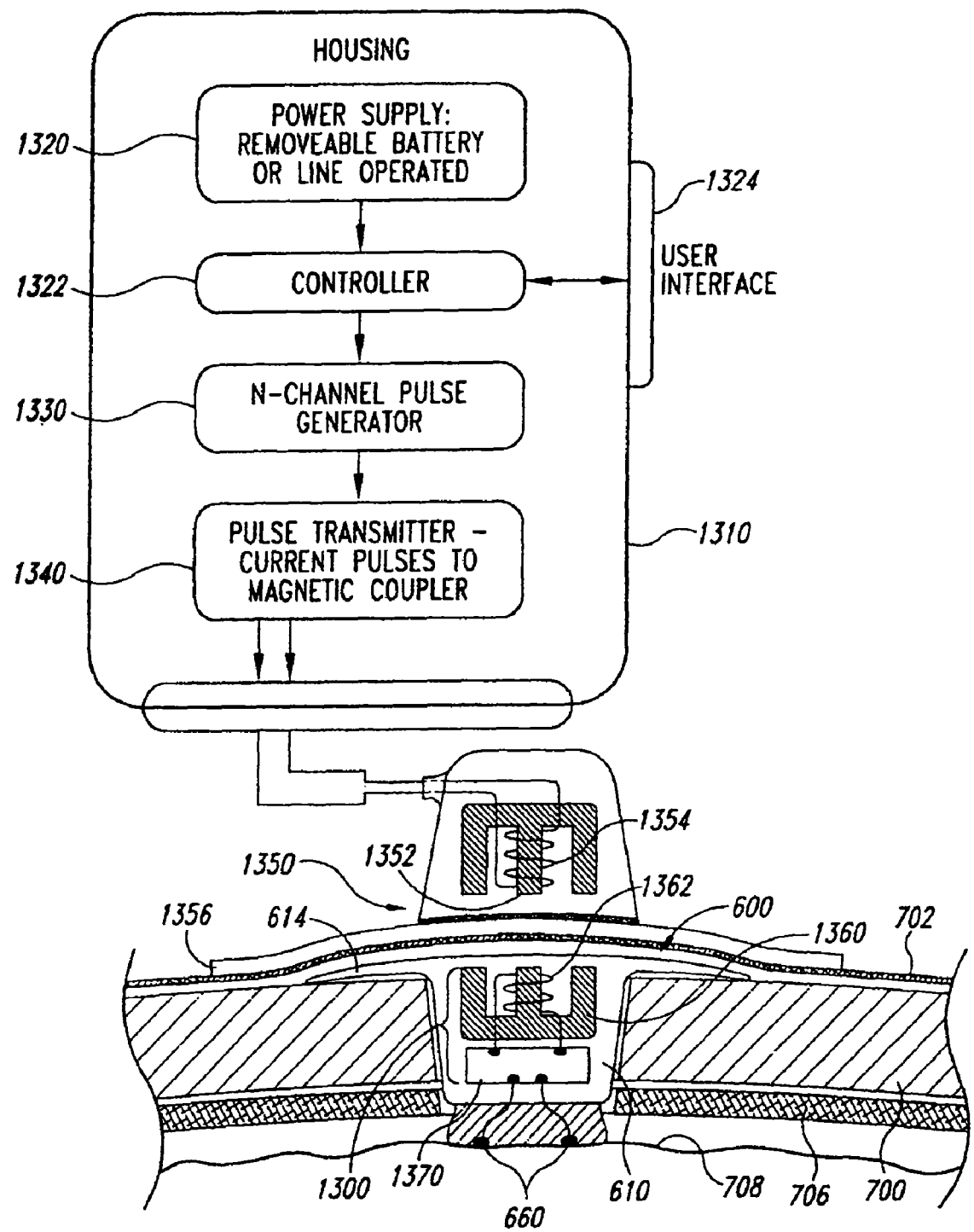
FIG. 13 is a cross-sectional view schematically illustrating a part of an implantable stimulation apparatus having a pulse system and an external controller in accordance with another embodiment of the invention.

FIG. 13 is a cross-sectional view of a pulse system 1300 for use in another embodiment of the implantable stimulation apparatus 600, together with an external controller 1310 for remotely controlling the pulse system 1300 externally from the patient using magnetic energy. In this embodiment, the external controller 1310 includes a power supply 1320, a controller 1322 coupled to the power supply 1320, and a user interface 1324 coupled to the controller 1322. The external controller 1310 can also include a pulse generator 1330 coupled to the controller 1332, a pulse transmitter 1340 coupled to the pulse generator 1330, and a magnetic coupler 1350 coupled to the pulse transmitter 1340. The magnetic coupler 1350 can include a ferrite core 1352 and a coil 1354 wrapped around a portion of the ferrite core 1352. The coil 1354 can also be electrically connected to the pulse transmitter 1340 so that electrical pulses applied to the coil 1354 generate changes in a corresponding magnetic field. The magnetic coupler 1350 can also include a flexible cap 1356 to position the magnetic coupler 1350 over the implanted stimulation apparatus 600.

The pulse system 1300 can include a ferrite core 1360 and a coil 1362 wrapped around a portion of the ferrite core 1360. The pulse system 1310 can also include a pulse delivery system 1370 including a rectifier and a pulse former. In operation, the ferrite core 1360 and the coil 1362 convert the changes in the magnetic field generated by the magnetic coupler 1350 into electrical pulses that are sent to the pulse delivery system 1370. The electrodes 660 are coupled to the pulse delivery system 1370 so that electrical pulses corresponding to the electrical pulses generated by the pulse generator 1330 in the external controller 1310 are delivered to the stimulation site on the patient.

3. Electrode Configurations

Figure 21:
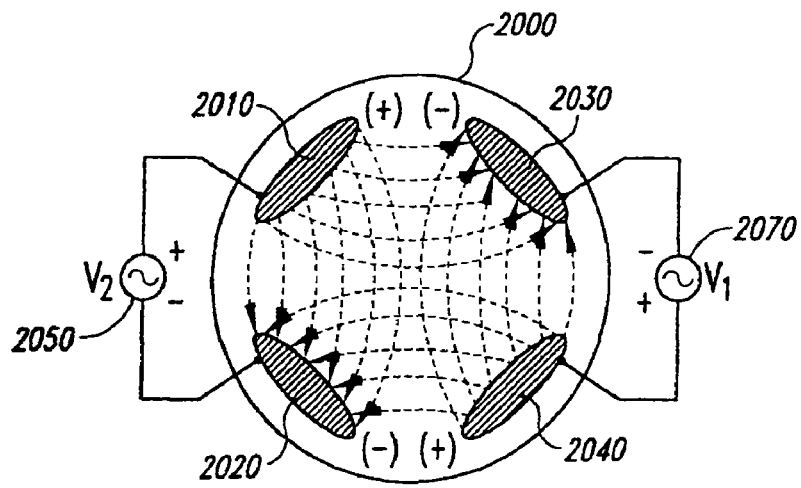
FIG. 21 is a bottom plan view of an electrode configuration for an implantable stimulation device in accordance with another embodiment of the invention.
Figure 22:
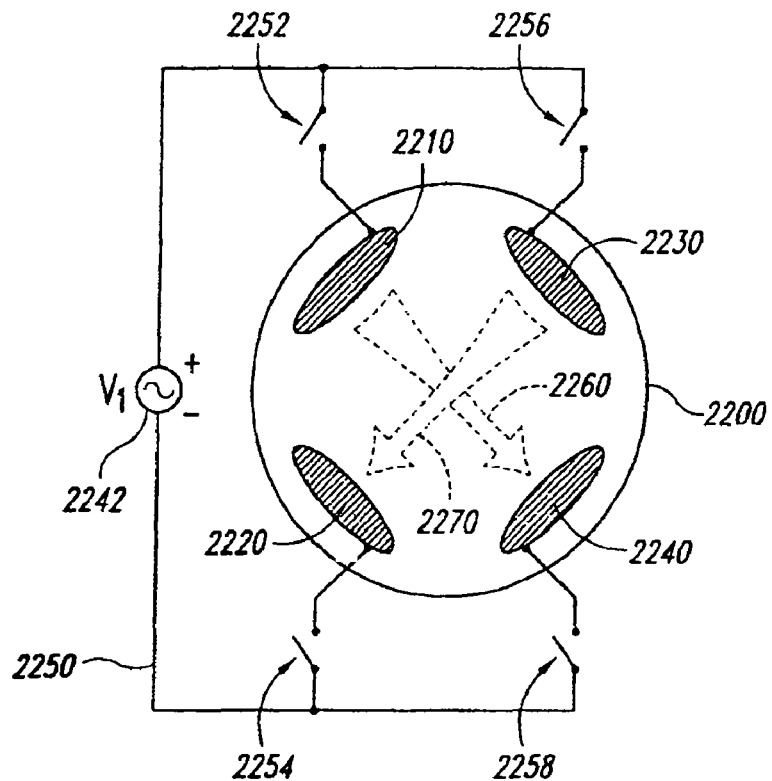
FIG. 22 is a bottom plan view of yet another embodiment of an electrode configuration for use with an implantable stimulation apparatus in accordance with the invention.
Figure 23:
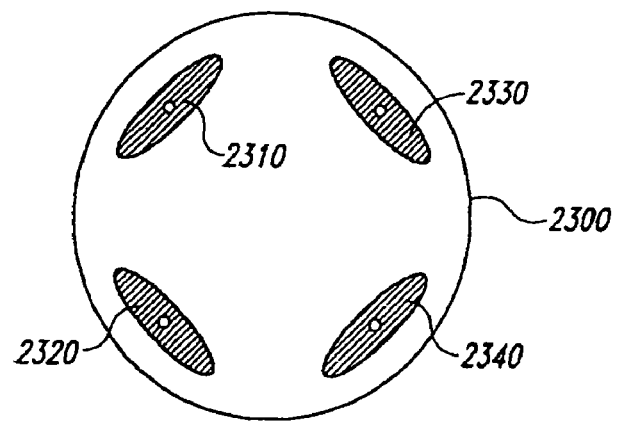
FIG. 23 is a bottom plan view.
Figure 24:
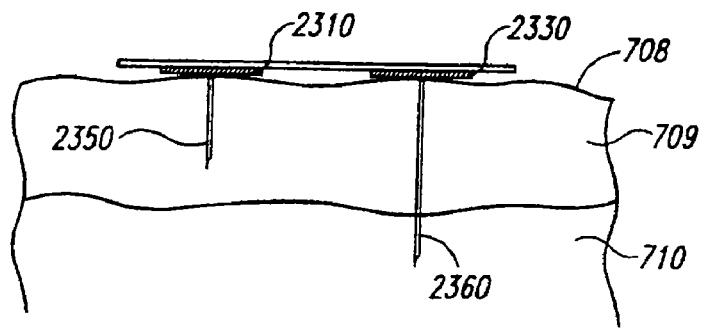
FIG. 24 is a cross-sectional view of an electrode configuration for use with a stimulation apparatus in accordance with still another embodiment of the invention.

FIGS. 14-24 illustrate electrodes in accordance with various embodiments of the invention that can be used with the stimulation apparatus disclosed herein. FIGS. 14-22 illustrate embodiments of electrodes configured to apply an electrical current to a stimulation site at least proximate to the pial surface of the cortex, and FIGS. 23 and 24 illustrate embodiments of electrodes configured to apply an electrical current within the cortex or below the cortex. It will be appreciated that other configurations of electrodes can also be used with other implantable stimulation apparatus.

Figure 14:
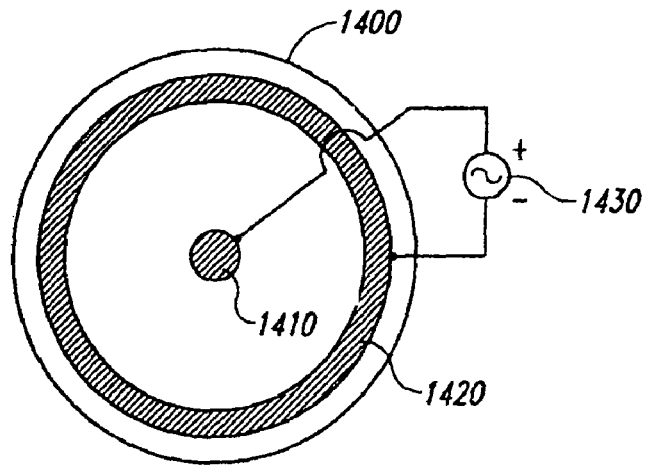
FIG. 14 is a bottom plan view and FIG. 15 is a cross-sectional view illustrating an electrode configuration for an implantable stimulation apparatus in accordance with an embodiment of the invention.
Figure 15:
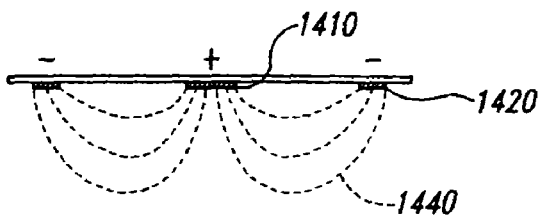

FIG. 14 is a bottom plan view and FIG. 15 is a cross-sectional view of a stimulation apparatus 1400 in accordance with an embodiment of the invention. In this embodiment, the stimulation apparatus 1400 includes a first electrode 1410 and a second electrode 1420 concentrically surrounding the first electrode 1410. The first electrode 1410 can be coupled to the positive terminal of a pulse generator 1430, and the second electrode 1420 can be coupled to the negative terminal of the pulse generator 1430. Referring to FIG. 15, the first and second electrodes 1410 and 1420 generate a toroidal electric field 1440.

Figure 16:
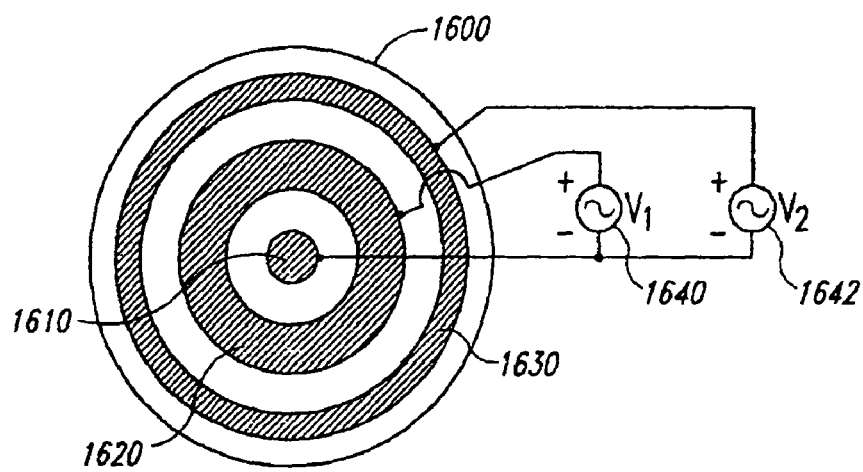
FIG. 16 is a bottom plan view and FIG. 17 is a cross-sectional view of an electrode configuration for an implantable stimulation apparatus in accordance with another embodiment of the invention.
Figure 17:
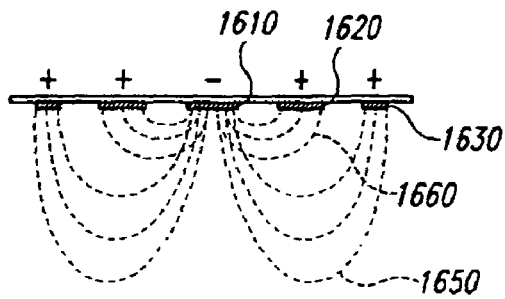

FIG. 16 is a bottom plan view and FIG. 17 is a cross-sectional view of a stimulation apparatus 1600 in accordance with another embodiment of the invention. In this embodiment, the stimulation apparatus 1600 includes a first electrode 1610, a second electrode 1620 surrounding the first electrode 1610, and a third electrode 1630 surrounding the second electrode 1620. The first electrode 1610 can be coupled to the negative terminals of a first pulse generator 1640 and a second pulse generator 1642; the second electrode 1620 can be coupled to the positive terminal of the first pulse generator 1640; and the third electrode 1630 can be coupled to the positive terminal of the second pulse generator 1642. In operation, the first electrode 1610 and the third electrode 1630 generate a first toroidal electric field 1650, and the first electrode the 1610 and the second electrode 1620 generate a second toroidal electric field 1660. The second toroidal electric field 1660 can be manipulated to vary the depth that the first toroidal electric field 1650 projects away from the base of the stimulation apparatus 1600.

Figure 18:
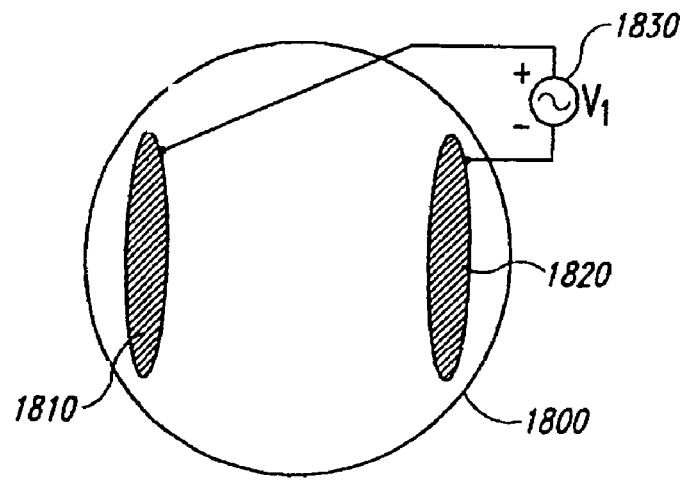
FIG. 18 is a bottom plan view and FIG. 19 is a cross-sectional view of an electrode configuration in accordance with yet another embodiment of the invention.
Figure 19:
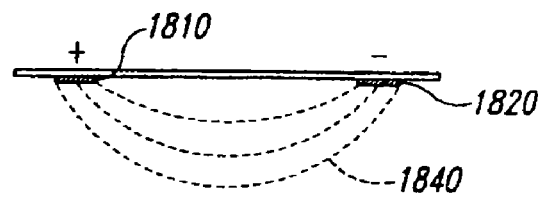

FIG. 18 is a bottom plan view and FIG. 19 is a cross-sectional view of a stimulation apparatus 1800 in accordance with yet another embodiment of the invention. In this embodiment, the stimulation apparatus 1800 includes a first electrode 1810 and a second electrode 1820 spaced apart from the first electrode 1810. The first and second electrodes 1810 and 1820 are linear electrodes which are coupled to opposite terminals of a pulse generator 1830. Referring to FIG. 19, the first and second electrodes 1810 and 1820 can generate an approximately linear electric field.

Figure 20:
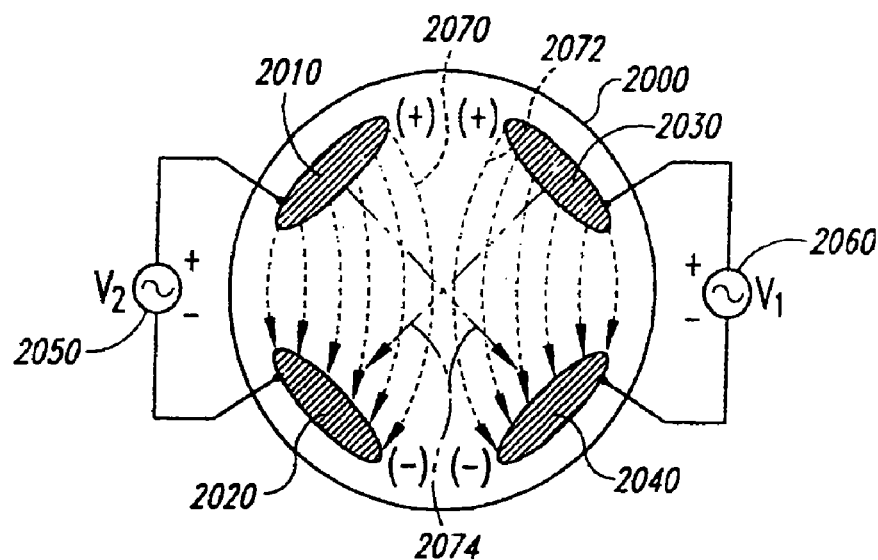
FIG. 20 is a bottom plan view of an electrode configuration for an implantable stimulation device in accordance with yet another embodiment of the invention.

FIG. 20 is a bottom plan view of a stimulation apparatus 2000 in accordance with still another embodiment of the invention. In this embodiment, the stimulation apparatus 2000 includes a first electrode 2010, a second electrode 2020, a third electrode 2030, and a fourth electrode 2040. The first and second electrodes 2010 and 2020 are coupled to a first pulse generator 2050, and the third and fourth electrodes 2030 and 2040 are coupled to a second pulse generator 2060. More specifically, the first electrode 2010 is coupled to the positive terminal and the second electrode 2020 is coupled to the negative terminal of the first pulse generator 2050, and the third electrode 2030 is coupled to the positive terminal and the fourth electrode 2040 is coupled to the negative terminal of the second pulse generator 2060. The first and second electrodes 2010 and 2020 are expected to generate a first electric field 2070, and the third and fourth electrodes 2030 and 2040 are expected to generate a second electric field 2072. It will be appreciated that the ions will be relatively free to move through the brain such that a number of ions will cross between the first and second electric fields 2070 and 2072 as shown by arrows 2074. This embodiment provides control of electric field gradients at the stimulation sites.

FIG. 21 is a bottom plan view of another embodiment of the stimulation apparatus 2000. In this embodiment, the first electrode 2010 is coupled to the positive terminal and the second electrode 2020 is coupled to the negative terminal of the first pulse generator 2050. In contrast to the embodiment shown in FIG. 20, the third electrode 2030 is coupled to the negative terminal and the fourth electrode 2040 is coupled to the positive terminal of the second pulse generator 2070. It is expected that this electrode arrangement will result in a plurality of electric fields between the electrodes. This allows control of the direction or orientation of the electric field.

FIG. 22 is a bottom plan view that schematically illustrates a stimulation apparatus 2200 in accordance with still another embodiment of the invention. In this embodiment, the stimulation apparatus 2200 includes a first electrode 2210, a second electrode 2220, a third electrode 2230, and a fourth electrode 2240. The electrodes are coupled to a pulse generator 2242 by a switch circuit 2250. The switch circuit 2250 can include a first switch 2252 coupled to the first electrode 2210, a second switch 2254 coupled to the second electrode 2220, a third switch 2256 coupled to the third electrode 2230, and a fourth switch 2258 coupled to the fourth electrode 2240. In operation, the switches 2252-2258 can be opened and closed to establish various electric fields between the electrodes 2210-2240. For example, the first switch 2252 and the fourth switch 2258 can be closed in coordination with a pulse from the pulse generator 2242 to generate a first electric field 2260, and/or the second switch 2254 and the third switch 2256 can be closed in coordination with another pulse from the pulse generator 2242 to generate a second electric field 2270. The first and second electric fields 2260 and 2270 can be generated at the same pulse to produce concurrent fields or alternating pulses to produce alternating or rotating fields.

FIG. 23 is a bottom plan view and FIG. 24 is a side elevational view of a stimulation apparatus 2300 in accordance with another embodiment of the invention. In this embodiment, the stimulation apparatus 2300 has a first electrode 2310, a second electrode 2320, a third electrode 2330, and a fourth electrode 2340. The electrodes 2310-2340 can be configured in any of the arrangements set forth above with reference to FIGS. 14-22. The electrodes 2310-2340 also include electrically conductive pins 2350 and/or 2360. The pins 2350 and 2360 can be configured to extend below the pial surface of the cortex. For example, because the length of the pin 2350 is less than the thickness of the cortex 709, the tip of the pin 2350 will accordingly conduct the electrical pulses to a stimulation site within the cortex 709 below the pial surface. The length of the pin 2360 is greater than the thickness of the cortex 709 to conduct the electrical pulses to a portion of the brain below the cortex 709, such as a deep brain region 710. The lengths of the pins are selected to conduct the electrical pulses to stimulation sites below the pia mater 708. As such, the length of the pins 2350 and 2360 can be the same for each electrode or different for individual electrodes. Additionally, only a selected portion of the electrodes and the pins can have an exposed conductive area. For example, the electrodes 2310-2340 and a portion of the pins 2350 and 2360 can be covered with a dielectric material so that only exposed conductive material is at the tips of the pins. It will also be appreciated that the configurations of electrodes set forth in FIGS. 14-22 can be adapted to apply an electrical current to stimulation sites below the pia mater by providing pin-like electrodes in a matter similar to the electrodes shown in FIGS. 23 and 24.

Several embodiments of the stimulation apparatus described above with reference to FIGS. 6-24 are expected to be more effective than existing transcranial or subcranial stimulation devices. In addition to positioning the electrodes under the skull, many embodiments of the stimulation apparatus described above also accurately focus the electrical energy in desired patterns relative to the pia mater 708, the dura mater 706, and/or the cortex 709. It will be appreciated that transcranial devices may not accurately focus the energy because the electrodes or other types of energy emitters are positioned relatively far from the stimulation sites and the skull diffuses some of the energy. Also, existing subcranial devices generally merely place the electrodes proximate to a specific nerve, but they do not provide electrode configurations that generate an electrical field in a pattern designed for the stimulation site. Several of the embodiments of the stimulation apparatus described above with reference to FIGS. 6-24 overcome this drawback because the electrodes can be placed against the neurons at the desired stimulation site. Additionally, the electrode configurations of the stimulation apparatus can be configured to provide a desired electric field that is not diffused by the skull 700. Therefore, several embodiments of the stimulation apparatus in accordance with the invention are expected to be more effective because they can accurately focus the energy at the stimulation site.

4. Implantable Stimulation Apparatus with Biasing Elements

FIGS. 25-30 illustrate several embodiments of stimulation apparatus having a biasing element in accordance with a different aspect of the invention. The stimulation apparatus shown in FIGS. 25-30 can be similar to those described above with reference to FIGS. 6-24. Therefore, the embodiments of the stimulation apparatus shown in FIGS. 25-30 can have the same pulse systems, support members and electrode configurations described above with reference to FIGS. 6-24.

Figure 25:
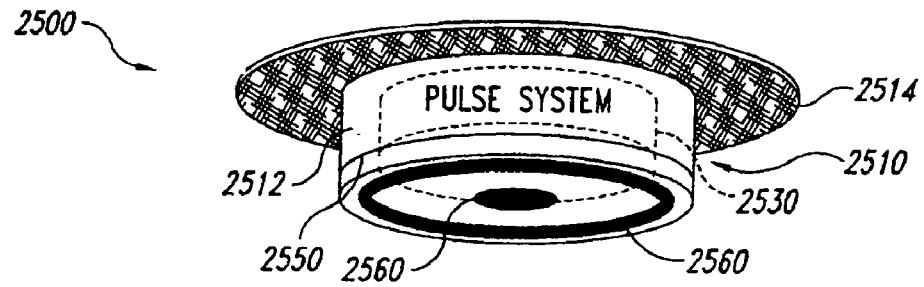
FIG. 25 is an isometric view schematically illustrating a part of an implantable stimulation apparatus with a mechanical biasing element in accordance with an embodiment of the invention.
Figure 26:
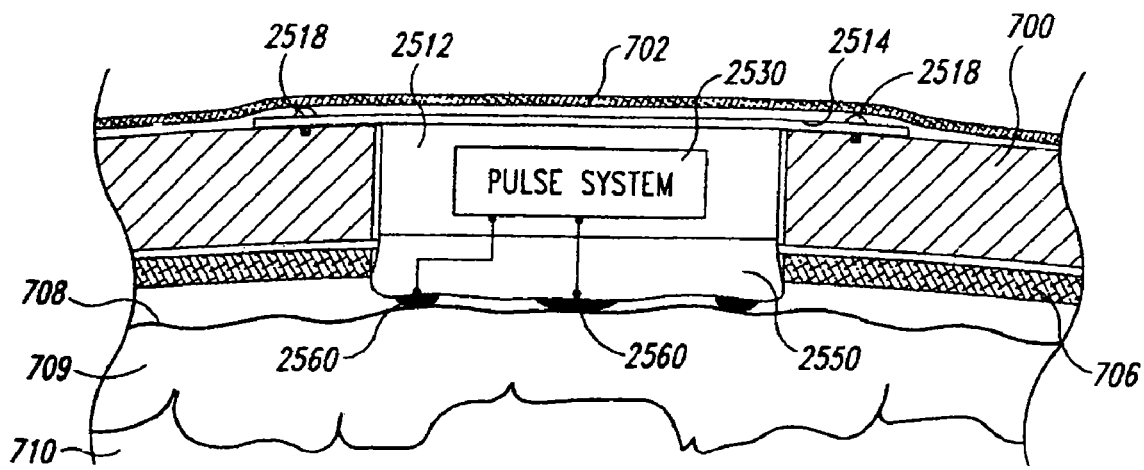
FIG. 26 is a cross-sectional view of a stimulation apparatus having a mechanical biasing element that has been implanted into a skull of a patient in accordance with an embodiment of the invention.

FIG. 25 is an isometric view and FIG. 26 is a cross-sectional view of a stimulation apparatus 2500 in accordance with an embodiment of the invention. In one embodiment, the stimulation apparatus 2500 includes a support member 2510, a pulse-system 2530 carried by the support member 2510, and first and second electrodes 2560 coupled to the pulse system 2530. The support member 2510 can be identical or similar to the support member 610 described above with reference to FIGS. 6 and 7. The support member 2510 can accordingly include a housing 2512 configured to be implanted in the skull 700 and an attachment element 2514 configured to be connected to the skull 700 by fasteners 2518 (FIG. 2), an adhesive, and/or an anchor. The pulse system 2530 can be identical or similar to any of the pulse systems described above with reference to FIGS. 6-13, and the first and second electrodes 2560 can have any of the electrode configurations explained above with reference to FIGS. 14-24. Unlike the stimulation apparatus described above, however, the stimulation apparatus 2500 includes a biasing element 2550 coupled to the electrodes 2560 to mechanically bias the electrodes 2560 away from the support member 2510. In an alternative embodiment, the biasing element 2550 can be positioned between the housing 2512 and the attachment element 2514, and the electrodes 2560 can be attached directly to the housing 2512. As explained in more detail below, the biasing element 2550 can be a compressible member, a fluid filled bladder, a spring, or any other suitable element that resiliently and/or elastically drives the electrodes 2560 away from the support member 2510.

FIG. 26 illustrates an embodiment of the stimulation apparatus 2500 after it has been implanted into the skull 700 of a patient. When the fasteners 2518 are attached to the skull 700, the biasing element 2550 should be compressed slightly so that the electrodes 2560 contact the stimulation site. In the embodiment shown in FIG. 26, the compressed biasing element 2550 gently presses the electrodes 2560 against the surface of the pia mater 708. It is expected that the biasing element 2550 will provide a uniform, consistent contact between the electrodes 2560 and the pial surface of the cortex 709. The stimulation apparatus 2500 is expected to be particularly useful when the implantable device is attached to the skull and the stimulation site is on the pia mater 708 or the dura mater 706. It can be difficult to position the contacts against the pia mater 708 because the distance between the skull 700, the dura mater 706, and the pia mater 708 varies within the cranium as the brain moves relative to the skull, and also as the depth varies from one patient to another. The stimulation apparatus 2500 with the biasing element 2550 compensates for the different distances between the skull 700 and the pia mater 708 so that a single type of device can inherently fit several different patients. Moreover, the stimulation apparatus 2500 with the biasing element 2550 adapts to changes as the brain moves within the skull. In contrast to the stimulation apparatus 2500 with the biasing element 2550, an implantable device that does not have a biasing element 2550 may not fit a particular patient or may not consistently provide electrical contact to the pia mater.

Figure 27:
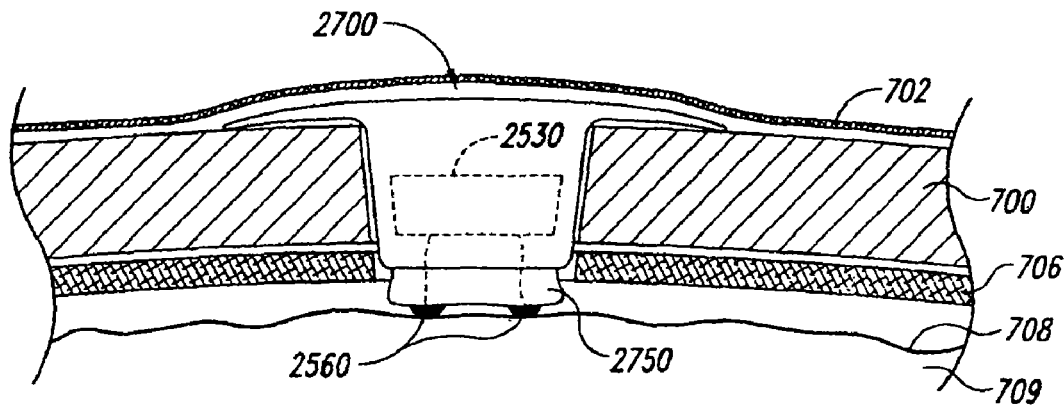
FIG. 27 is a cross-sectional view schematically illustrating a part of a stimulation apparatus having a biasing element in accordance with an embodiment of the invention.
Figure 28:
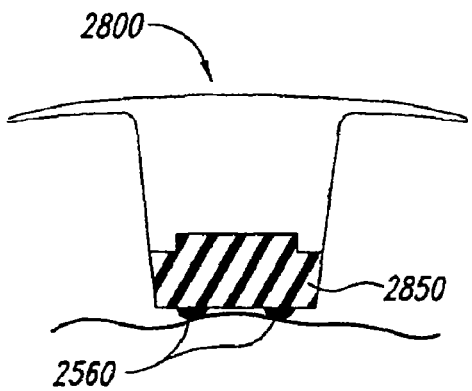
FIG. 28 is a cross-sectional view of a stimulation apparatus having a biasing element in accordance with still another embodiment of the invention.

FIGS. 27 and 28 are cross-sectional views of stimulation apparatus in which the biasing elements are compressible members. FIG. 27, more specifically, illustrates a stimulation apparatus 2700 having a biasing element 2750 in accordance with an embodiment of the invention. The stimulation apparatus 2700 can have an integrated pulse system 2530 and electrodes 2560 coupled to the pulse system 2530 in a manner similar to the stimulation apparatus 2500. The biasing element 2750 in this embodiment is a compressible foam, such as a biocompatible closed cell foam or open cell foam. As best shown in FIG. 27, the biasing element 2750 compresses when the stimulation apparatus 2700 is attached to the skull. FIG. 28 illustrates a stimulation apparatus 2800 having a biasing element 2850 in accordance with another embodiment of the invention. The biasing element 2850 can be a compressible solid, such as silicon rubber or other suitable compressible materials. The electrodes 2560 are attached to the biasing element 2850.

Figure 29:
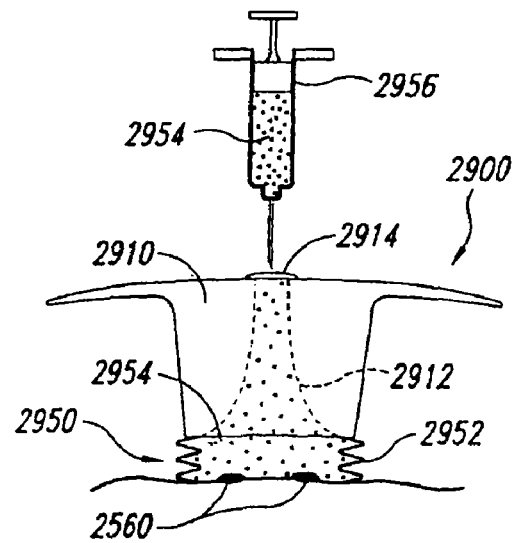
FIG. 29 is a cross-sectional view of a stimulation apparatus having a biasing element in accordance with yet another embodiment of the invention.

FIG. 29 is a cross-sectional view of a stimulation apparatus 2900 having a biasing element 2950 in accordance with another embodiment of the invention. The stimulation apparatus 2900 can have a support member 2910 including an internal passageway 2912 and a diaphragm 2914. The biasing element 2950 can include a flexible bladder 2952 attached to the support member 2910, and the electrodes 2560 can be attached to the flexible bladder 2952. In operation, the flexible bladder 2952 is filled with a fluid 2954 until the electrodes 2560 press against the stimulation site. In one embodiment, the flexible bladder 2952 is filled by inserting a needle of a syringe 2956 through the diaphragm 2914 and injecting the fluid 2954 into the internal passageway 2912 and the flexible bladder.

Figure 30:
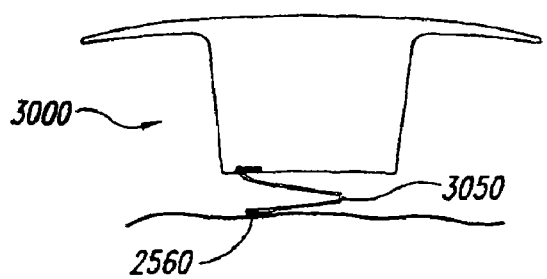
FIG. 30 is a cross-sectional view of a stimulation apparatus having a biasing element in accordance with yet another embodiment of the invention.

FIG. 30 is a cross-sectional view of a stimulation apparatus 3000 having a biasing element 3050 in accordance with another embodiment of the invention. In this embodiment, the biasing element 3050 is a spring and the electrodes 2560 are attached to the spring. The biasing element 3050 can be a wave spring, a leaf spring, or any other suitable spring that can mechanically bias the electrodes 2560 against the stimulation site.

Although several embodiments of the stimulation apparatus shown in FIGS. 25-30 can have a biasing element and any of the pulse systems set forth above with respect to FIGS. 6-13, it is not necessary to have a pulse system contained within the support member. Therefore, certain embodiments of implantable stimulation apparatus in accordance with the invention can have a pulse system and/or a biasing member in any combination of the embodiments set forth above with respect to FIGS. 6-30.

5. Implantable Stimulation Apparatus with External Pulse Systems

Figure 31:
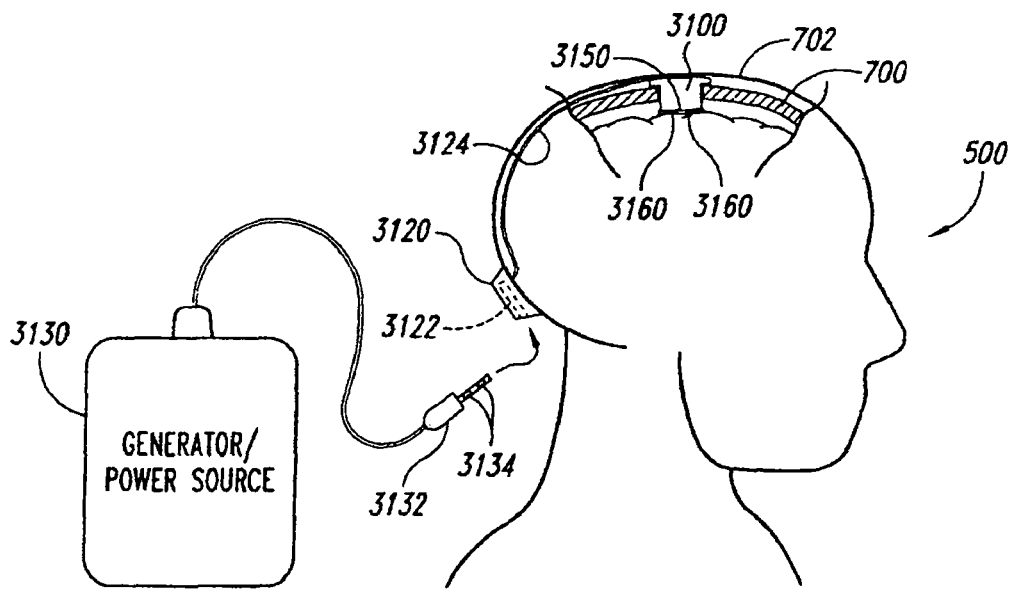
FIG. 31 is a cross-sectional view schematically illustrating a portion of an implantable stimulation apparatus having an external power source and pulse generator in accordance with an embodiment of the invention.

FIGS. 31-35 are schematic cross-sectional views of various embodiments of implantable stimulation apparatus having external pulse systems. FIG. 31, more specifically, illustrates an embodiment of a stimulation apparatus 3100 having a biasing element 3150 to which a plurality of electrodes 3160 are attached in a manner similar to the stimulation apparatus described above with reference to FIGS. 25-30. It will be appreciated that the stimulation apparatus 3100 may not include the biasing element 3150. The stimulation apparatus 3100 can also include an external receptacle 3120 having an electrical socket 3122 and an implanted lead line 3124 coupling the electrodes 3160 to contacts (not shown) in the socket 3122. The lead line 3124 can be implanted in a subcutaneous tunnel or other passageway in a manner known to a person skilled and art.

The stimulation apparatus 3100, however, does not have an internal pulse system carried by the portion of the device that is implanted in the skull 700 of the patient 500. The stimulation apparatus 3100 receives electrical pulses from an external pulse system 3130. The external pulse system 3130 can have an electrical connector 3132 with a plurality of contacts 3134 configured to engage the contacts within the receptacle 3120. The external pulse system 3130 can also have a power supply, controller, pulse generator, and pulse transmitter to generate the electrical pulses. In operation, the external pulse system 3130 sends electrical pulses to the stimulation apparatus 3100 via the connector 3132, the receptacle 3120, and the lead line 3124.

Figure 32:
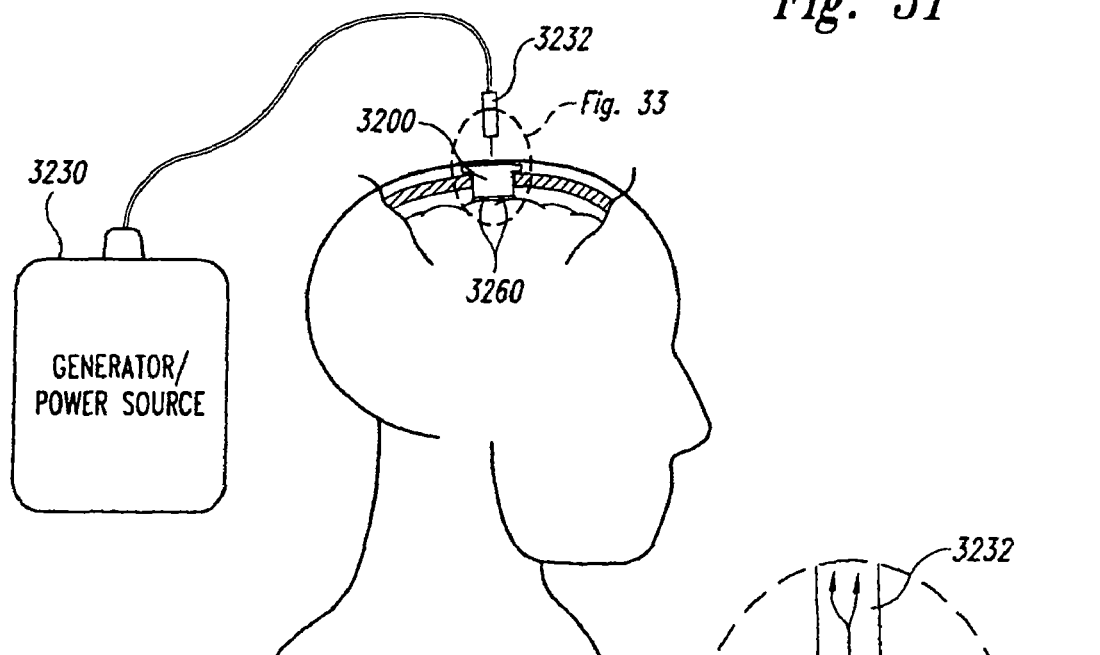
FIG. 32 is a cross-sectional view schematically illustrating a portion of an implantable stimulation apparatus having an external power source and pulse generator in accordance with another embodiment of the invention.
Figure 33:
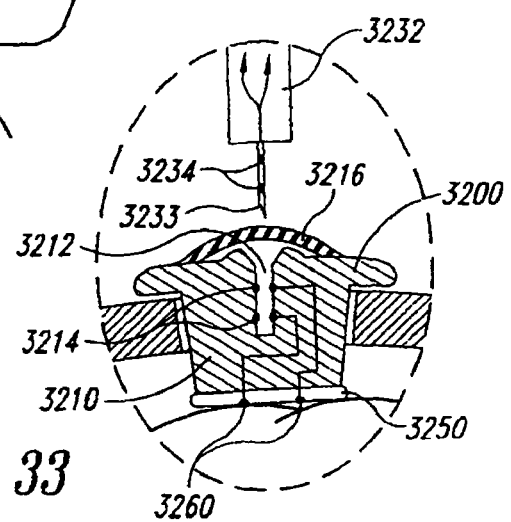
FIG. 33 is a cross-sectional view illustrating in greater detail a portion of the implantable stimulation apparatus of FIG. 32.

FIGS. 32 and 33 illustrate an embodiment of a stimulation apparatus 3200 for use with an external pulse system in accordance with another embodiment of the invention. Referring to FIG. 33, the stimulation apparatus 3200 can include a support structure 3210 having a socket 3212, a plurality of contacts 3214 arranged in the socket 3212, and a diaphragm 3216 covering the socket 3212. The stimulation apparatus 3200 can also include a biasing element 3250 and a plurality of electrodes 3260 attached to the biasing element 3250. Each electrode 3260 is directly coupled to one of the contacts 3214 within the support structure 3210. It will be appreciated that an alternative embodiment of the stimulation apparatus 3200 does not include the biasing element 3250.

Referring to FIGS. 32 and 33 together, the stimulation apparatus 3200 receives the electrical pulses from an external pulse system 3230 that has a power supply, controller, pulse generator, and pulse transmitter. The external pulse system 3230 can also include a plug 3232 having a needle 3233 (FIG. 33) and a plurality of contacts 3234 (FIG. 33) arranged on the needle 3233 to contact the internal contacts 3214 in the socket 3212. In operation, the needle 3233 is inserted into the socket 3212 to engage the contacts 3234 with the contacts 3214, and then the pulse system 3230 is activated to transmit electrical pulses to the electrodes 3260.

Figure 34:
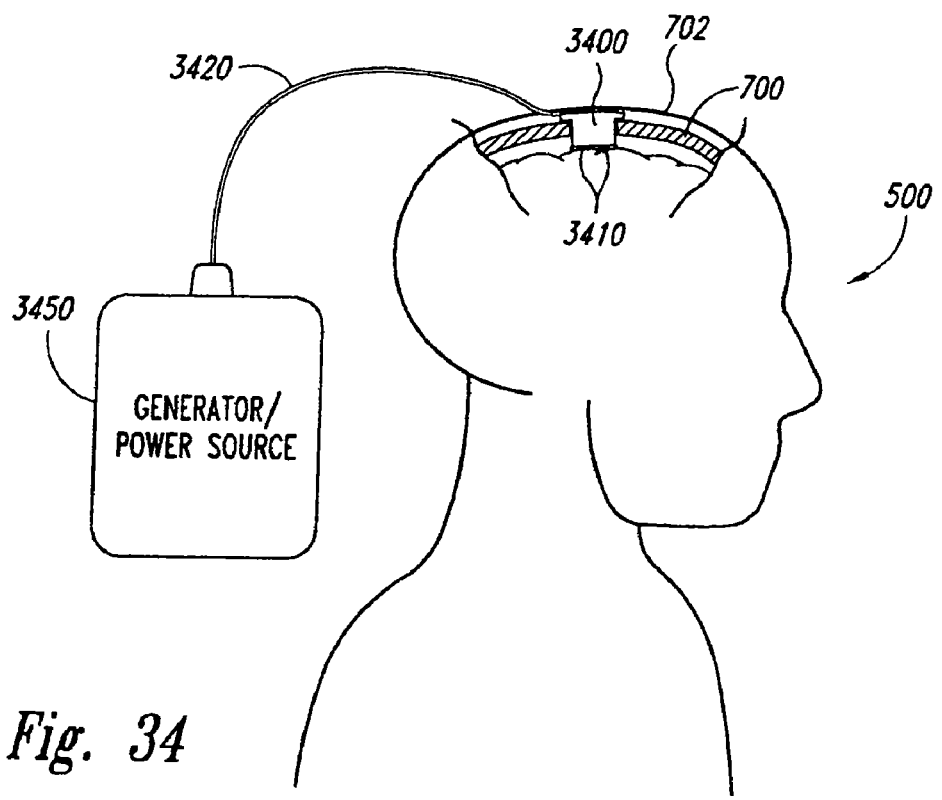
FIG. 34 is a cross-sectional view schematically illustrating a portion of an implantable stimulation apparatus and an external controller in accordance with another embodiment of the invention.
Figure 35:
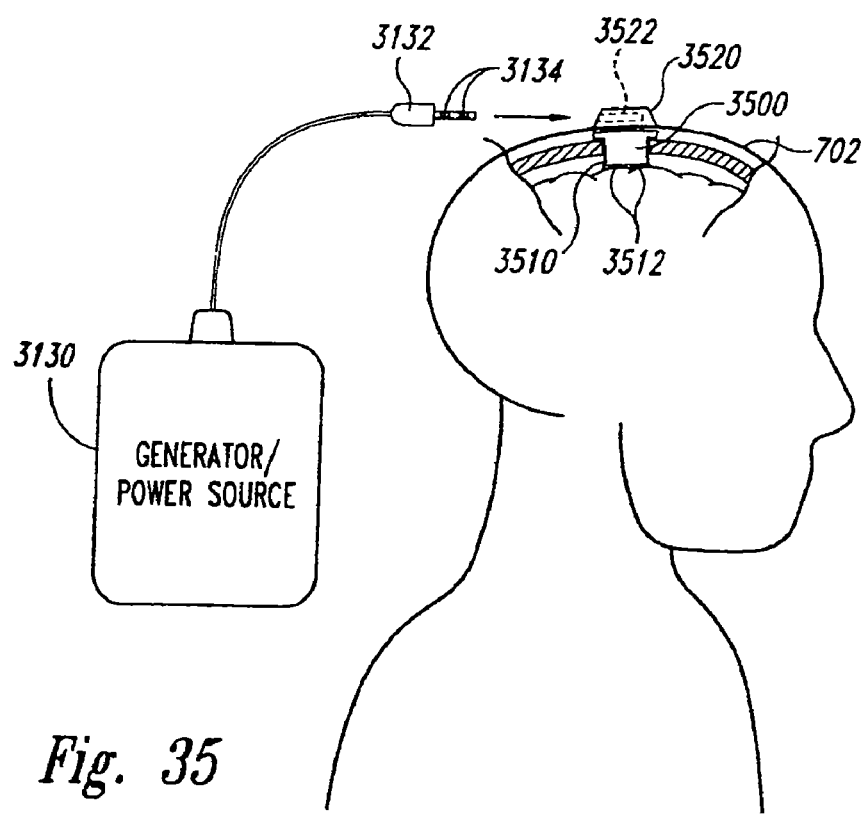
FIG. 35 is a cross-sectional view schematically illustrating a portion of an implantable stimulation apparatus and an external controller in accordance with yet another embodiment of the invention.

FIGS. 34 and 35 illustrate additional embodiments of stimulation apparatus for use with external pulse systems. FIG. 34 illustrates an embodiment of a stimulation apparatus 3400 having electrodes 3410 coupled to a lead line 3420 that extends under the scalp 702 of the patient 500. The lead line 3420 is coupled to an external pulse system 3450. FIG. 35 illustrates an embodiment of a stimulation apparatus 3500 having a support member 3510, electrodes 3512 coupled to the support member 3510, and an external receptacle 3520 mounted on the scalp 702. The external receptacle 3520 can also be connected to the support member 3510. The external receptacle 3520 can have a socket 3522 with contacts (not shown) electrically coupled to the electrodes 3512. The stimulation apparatus 3500 can be used with the external pulse system 3130 described above with reference to FIG. 31 by inserting the plug 3132 into the socket 3522 until the contacts 3134 on the plug 3132 engage the contacts within the socket 3522.

6. Alternate Embodiments of Implantable Stimulation Apparatus

Figure 36:
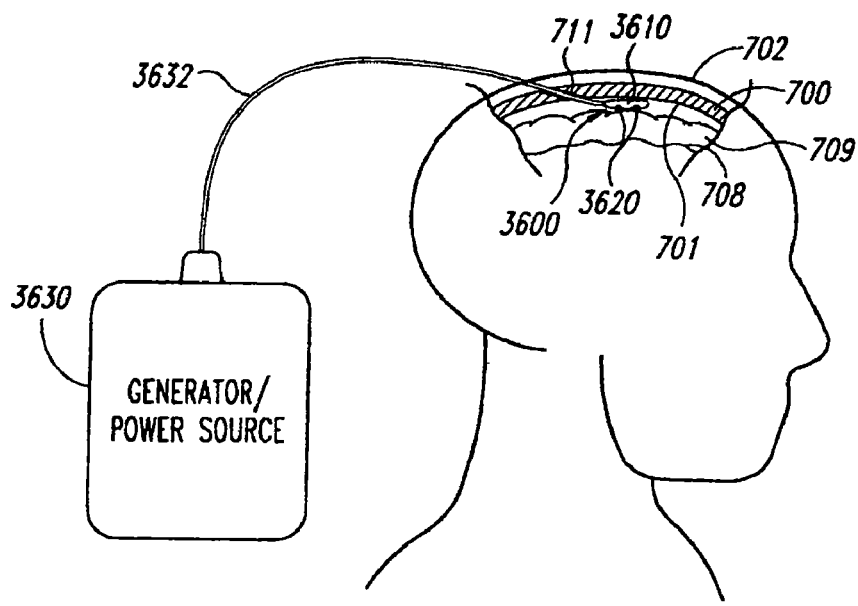
FIG. 36 is a cross-sectional view schematically illustrating a portion of an implantable stimulation apparatus in accordance with yet another embodiment of the invention.

FIG. 36 is a schematic cross-sectional view of an implantable stimulation apparatus 3600 in accordance with another embodiment of the invention. In one embodiment, the stimulation apparatus 3600 has a support structure 3610 and a plurality of electrodes 3620 coupled to the support structure 3610. The support structure 3610 can be configured to be implanted under the skull 700 between an interior surface 701 of the skull 700 and the pial surface of the brain. The support structure 3610 can be a flexible or compressible body such that the electrodes 3620 contact the pia mater 708 when the stimulation apparatus 3600 is implanted under the skull 700. In other embodiments, the support structure 3610 can position the electrodes 3620 so that they are proximate to, but not touching, the pia mater 708.

In one embodiment, the stimulation apparatus 3600 can receive electrical pulses from an external controller 3630. For example, the external controller 3630 can be electrically coupled to the stimulation apparatus 3600 by a lead line 3632 that passes through a hole 711 in the skull 700. In an alternative embodiment, the stimulation apparatus 3600 can include an integrated pulse system similar to the pulse systems described above with reference to FIGS. 6-13. Such an embodiment of the stimulation apparatus 3600 can accordingly use a wireless external control unit. It will be appreciated that the electrodes 3620 of the stimulation apparatus 3600 can have several of the electrode configurations described above with reference to FIGS. 14-24.

Figure 37:
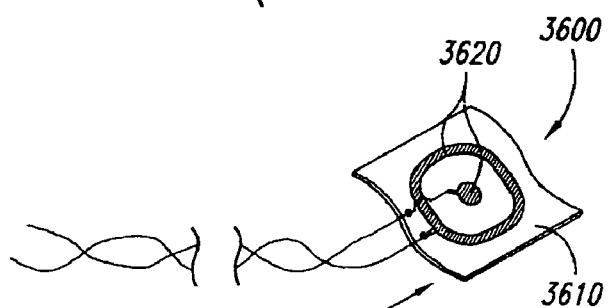
FIG. 37 is an isometric view.
Figure 38:
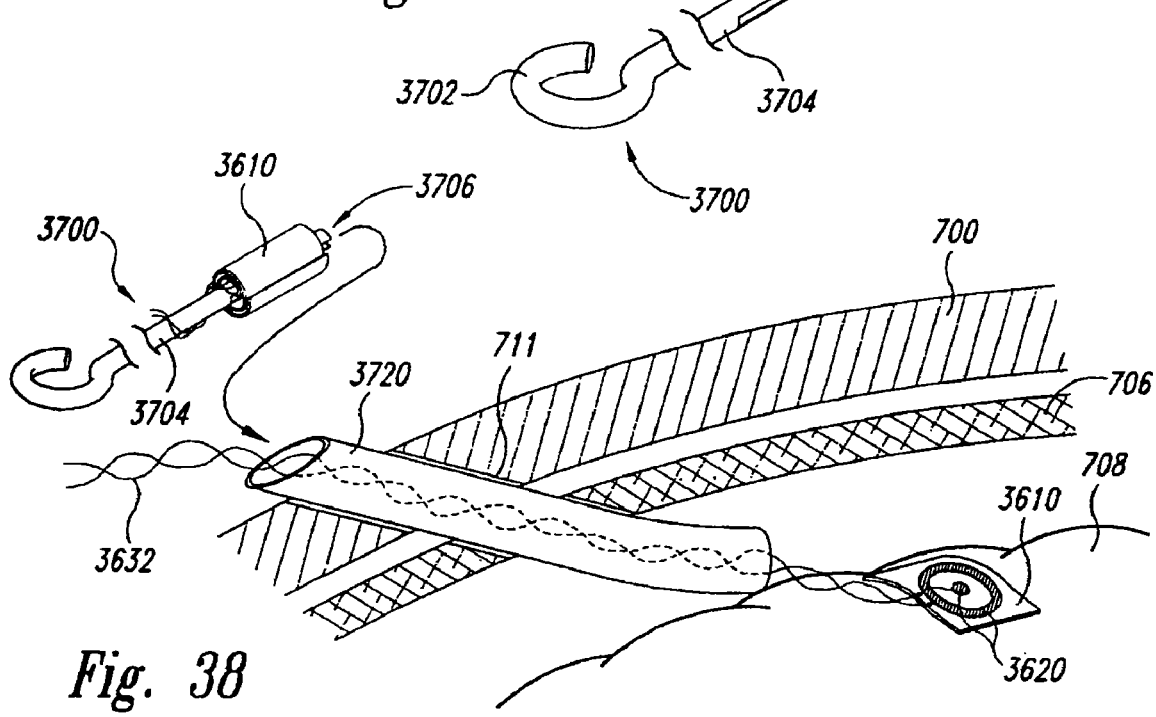
FIG. 38 is a cross-sectional view illustrating an implantable stimulation apparatus in accordance with an embodiment of the invention.

FIGS. 37 and 38 illustrate one embodiment of the implantable stimulation apparatus 3600. Referring to FIG. 37, the support structure 3610 can be a flexible substrate and the electrodes 3620 can be conductive elements that are printed onto the flexible substrate. The stimulation apparatus 3600, for example, can be manufactured in a manner similar to flexible printed circuit assemblies that are used in electrical components. The stimulation apparatus 3600 can be implanted under the skull 700 using an insertion tool 3700. In one embodiment, the insertion tool 3700 has a handle 3702 and a shaft 3704 projecting from the handle 3702. The shaft 3704 can have a slot 3706 configured to receive a flat portion of the support member 3610. Referring to FIG. 38, the support member 3610 is wrapped around the shaft 3704, and then the stimulation apparatus 3600 is passed to a tube 3720 positioned in the hole 711 through the scalp 700 and the dura mater 706. After the stimulation apparatus 3600 has been passed through the tube 3720, it is unfurled to place the electrodes 3620 at least proximate to the pia mater 708. The electrodes 3620 can be coupled to an external controller by the lead lines 3632.

Figure 39:
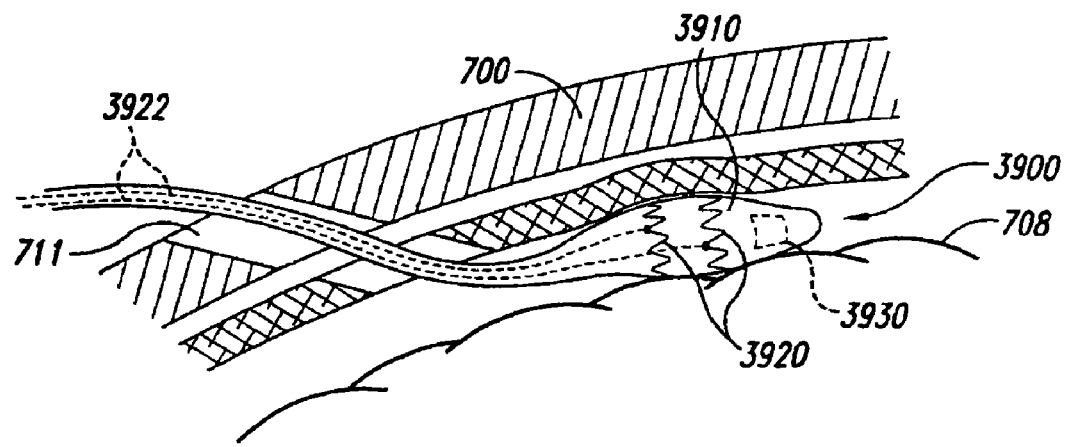
FIG. 39 is a cross-sectional view illustrating an implantable stimulation apparatus in accordance with yet another embodiment of the invention.

FIG. 39 illustrates another embodiment of an implantable stimulation apparatus 3900 that is also configured to be positioned between the skull 700 and the pia mater 708. In one embodiment, the stimulation apparatus 3900 can include a support member 3910 and a plurality of electrodes 3920 coupled to the support member 3910. The electrodes 3920 can be coupled to individual lead lines 3922 to connect the electrodes 3920 to an external pulse system. In an alternative embodiment, an integrated pulse system 3930 can be carried by the support member 3910 so that the electrodes 3920 can be coupled directly to the integrated pulse system 3930 without external lead lines 3922. The support member 3910 can be a resiliently compressible member, an inflatable balloon-like device, or a substantially solid incompressible body. In the particular embodiment shown in FIG. 39, the support member 3910 is an inflatable balloon-like device that carries the electrodes 3920. In operation, the stimulation apparatus 3900 is implanted by passing the distal end of the support member 3910 through the hole 711 in the skull 700 until the electrodes 3920 are positioned at a desired stimulation site.

Figure 40:
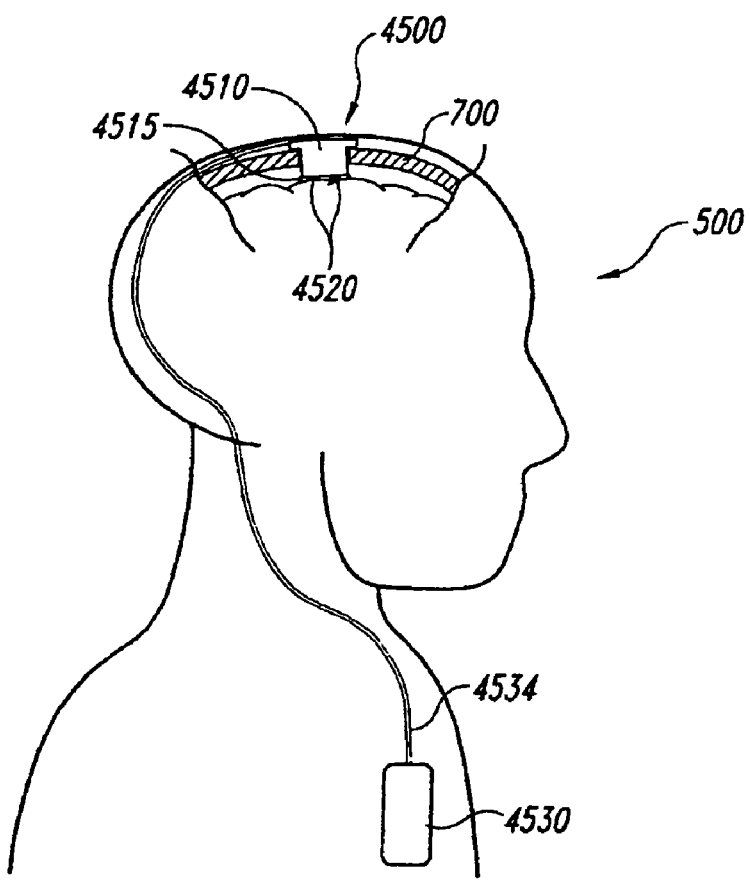
FIG. 40 is a schematic illustration of an implantable stimulation apparatus in accordance with an embodiment of the invention.

FIG. 40 is a schematic illustration of a stimulation apparatus 4000 together with an internal pulse system 4030 in accordance with another embodiment of the invention. The stimulation apparatus 4000 can include a support member 4010, a biasing element 4015 carried by the support member 4010, and a plurality of electrodes 4020 carried by the biasing element 4015. The internal pulse system 4030 can be similar to any of the integrated pulse systems described above with reference to FIGS. 6-13, but the internal pulse system 4030 is not an integrated pulse system because it is not carried by the housing 4010. The internal pulse system 4030 can be coupled to the electrodes 4020 by a cable 4034. In a typical application, the cable 4034 is implanted subcutaneously in a tunnel from a subclavicular region, along the back of the neck, and around the skull. The stimulation apparatus 4000 can also include any of the electrode configurations described above with reference to FIGS. 14-24.

Figure 41A:
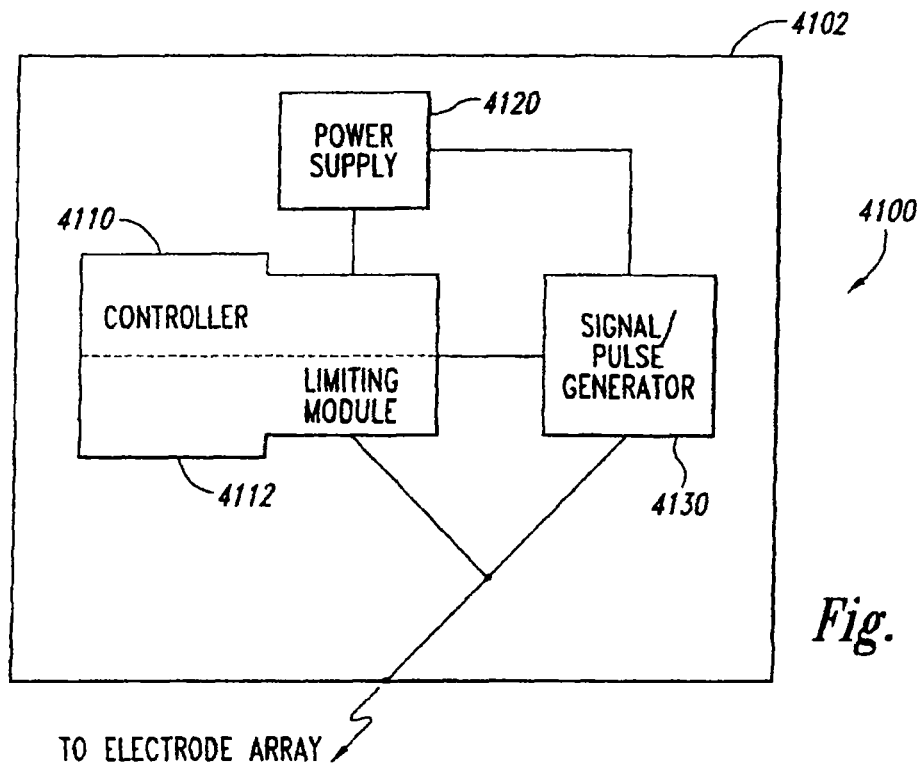
FIGS. 41A and 41B are schematic illustrations of stimulation units in accordance with other embodiments of the invention.

FIG. 41A is a schematic view illustrating a stimulation apparatus 4100 suitable for performing the stimulation procedures 106 described above with reference to FIGS. 5C and 5D. The stimulation apparatus 4100 includes a housing 4102 that is configured to be implanted in or otherwise attached to the patient. The housing 4102, for example, can be any of the structures described above for being implanted in the patient's cranium or another area located above the patient's neck. In other embodiments, the housing 4102 can be configured to be implanted below the patient's neck, such as a subclavicular or abdominal location.

The stimulation apparatus 4100 illustrated in FIG. 41A includes a controller 4110, a power supply 4120, and a signal or pulse generator 4130. The power supply 4120 and the signal generator 4130 are coupled to the controller 4110, and the signal generator 4130 is also coupled to the power supply 4120. The stimulation apparatus 4100 further includes a limiting module 4112 that can be a component of the controller 4110 or a separate standalone component. The limiting module 4112 prevents stimulation signals generated by the signal generator 4130 from being provided to an electrode array after expiration of a therapy period. As explained above, the therapy period is the period of one or more therapy sessions that constitute a complete therapy treatment for effectuating recovery of a functional ability corresponding to an impaired neural function.

The limiting module 4112 provides a limited duration treatment that terminates operation of the signal general 4130 or otherwise disconnects the signal generator 4130 from either the power supply 4120 or the electrode array. The limiting module 4112 can be a hardware or software switch. In one embodiment, the limiting module causes the controller 4110 to deactivate the signal generator 4130 so that the signal generator 4130 does not produce signals after expiration of the therapy period. The limiting module 4112 can also be a hardware or software switch in the controller 4110 that disconnects the power supply 4120 from the signal generator 4130. In another embodiment, the limiting module 4112 can be a hardware or software switch that disconnects the signal generator 4130 from the electrode array.

Figure 41B:
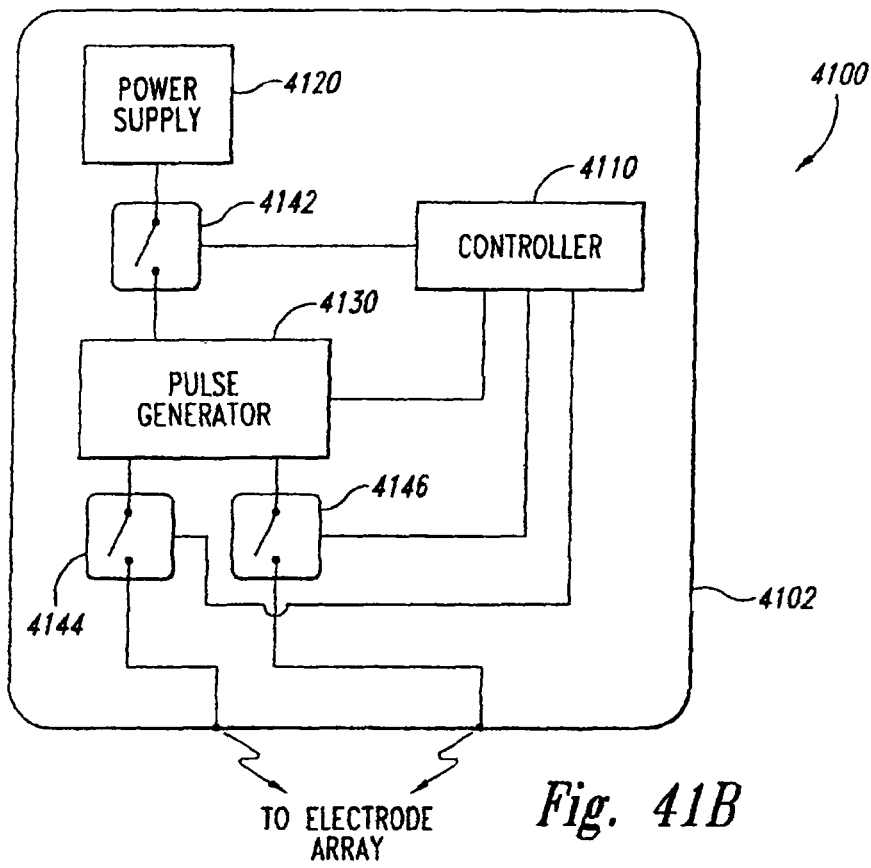

FIG. 41B is a schematic view illustrating particular examples of several embodiments of the stimulation apparatus 4100. In this embodiment, the limiting module comprises one or more switches 4142, 4144 and/or 4146 that are operated by the controller 4110. For example, the limiting module can include a switch 4142 between the power supply 4120 and the pulse generator 4130. The controller 4110 opens the switch 4142 to disconnect the power supply 4120 from the pulse generator 4130. In another embodiment, the limiting module can include a switch 4144 and/or a switch 4146 that disconnects the pulse generator 4130 from the electrode array. In any of these embodiments, the controller 4110 can operate these switches, or the switches can be operated by another mechanism that is either a component of the stimulation apparatus 4100 or an external devices. For example, the switches 4142, 4144, and/or 4146 can be operated telemetrically by a magnetic source or an RF source external to the patient for manual operation of the limiting module.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A method for treating a patient having brain damage associated with a stroke, comprising:
   applying electrical stimulation to the cortex of the patient's brain by positioning implanting at least one electrode beneath the patient's skull and on the dura such that at least one electrode is proximate to a target cortical stimulation site and applying electrical signals to the patient's brain via the at least one electrode;
   administering a test to determine the patient's physical abilities, cognitive abilities or a combination thereof after applying the electrical stimulation; and
   based at least in part on results of the test, performing at least one of the following functions:
   (a) changing at least one parameter in accordance with which the electrical stimulation is applied;
   (b) ceasing to apply the electrical stimulation; and
   (c) maintaining stimulation parameters in accordance with which the electrical stimulation is applied.

2. The method of claim 1 wherein administering the test is part of a patient evaluation that also includes exposing the patient to magnetic fields.

3. The method of claim 2 wherein exposing the patient to magnetic fields includes evaluating the functioning of the patient using magnetic resonance techniques.

4. The method of claim 1 wherein administering the test is part of a patient evaluation that also includes evaluating a physiologic function that corresponds to neuropsychological functioning of the patient.

5. The method of claim 1 wherein administering the test to the patient includes administering a test that elicits a cognitive response on the part of the patient.

6. The method of claim 1, further comprising directing the patient to engage in an adjunctive therapy.

7. The method of claim 6 wherein the adjunctive therapy is selected to include a cognitive task.

8. The method of claim 6 wherein the adjunctive therapy is selected to include a motor task.

9. The method of claim 6 wherein the adjunctive therapy is selected to include behavioral therapy.

10. The method of claim 6 wherein directing the patient to engage in an adjunctive therapy includes directing the patient to engage in an adjunctive therapy during a treatment session that also includes applying the electromagnetic stimulation.

11. The method of claim 1 wherein administering the test includes administering a cognitive test that results in a cognitive response and a motor response by the patient, and wherein the method further comprises distinguishing the cognitive response from the motor response.

12. The method of claim 1 wherein changing at least one parameter in accordance with which the electrical stimulation is applied includes changing a location at which the stimulation signal is applied.

13. The method of claim 1 wherein the damage is associated with the person's vision and visual perception.

14. A method for treating a post-stroke patient having a neglect disorder, comprising:
- identifying a cortical stimulation site by identifying one or more anatomical landmarks, identifying lesioned or other damaged areas, identifying areas adjacent or proximate to the damaged areas, and/or identifying other areas expected to assume, at least in part, the functions of a damaged area, or otherwise improve the functionality of the patient;
- positioning at least one electrode beneath the patient's skull and on the dura so that at least one electrode is at least proximate to the patient's cortex; and
- applying electrical stimulation to the patient's brain via the at least one electrode.

15. A method for treating a post-stroke patient having a cognitive disorder, comprising:
- identifying a cortical stimulation site by identifying one or more anatomical landmarks, identifying lesioned or other damaged areas, identifying areas adjacent or proximate to the damaged areas, and/or identifying other areas expected to assume, at least in part, the functions of a damaged area, or otherwise improve the functionality of the patient;
- positioning at least one electrode beneath the patient's skull and on the dura so that at least one electrode is at least proximate to the patient's cortex;
- applying electrical stimulation to the patient's brain via the at least one electrode;
- administering a test to determine the patient's cognitive abilities after applying the electrical stimulation; and
- based at least in part on results of the test, performing at least one of the following functions:
  - (a) changing at least one parameter in accordance with which the electrical stimulation is applied;
  - (b) ceasing to apply the electrical stimulation; and
  - (c) maintaining stimulation parameters in accordance with which the electrical stimulation is applied.

* * * * *